United States Patent [19]
Martin et al.

[11] Patent Number: 5,777,717
[45] Date of Patent: *Jul. 7, 1998

[54] METHOD FOR SIMULATION OF VISUAL DISABILITIES

[75] Inventors: Neil F. Martin, Potomac; Howard N. Robinson, Lutherville, both of Md.

[73] Assignee: Bloom & Kreten, Towson, Md.; a part interest

[*] Notice: The term of this patent shall not extend beyond the expiration date of Pat. No. 5,495,305.

[21] Appl. No.: 593,880

[22] Filed: Jan. 30, 1996

Related U.S. Application Data

[63] Continuation-in-part of Ser. No. 331,029, Oct. 27, 1994, Pat. No. 5,495,305.

[51] Int. Cl.$^6$ ........................................ G02C 7/04
[52] U.S. Cl. ................................................ 351/177
[58] Field of Search .......................... 351/160 R, 160 H, 351/161, 162, 177

[56] References Cited

U.S. PATENT DOCUMENTS

| | | | |
|---|---|---|---|
| 3,536,386 | 10/1970 | Spivack | 351/160 |
| 3,794,414 | 2/1974 | Wesley | 351/161 |
| 4,405,216 | 9/1983 | Nadler et al. | 351/237 |
| 4,698,022 | 10/1987 | Gilson | 351/47 |
| 4,890,911 | 1/1990 | Sulc et al. | 351/160 |
| 4,966,452 | 10/1990 | Shields et al. | 351/219 |
| 4,976,533 | 12/1990 | Hahn et al. | 351/160 |
| 5,009,497 | 4/1991 | Cohen | 351/161 |
| 5,062,701 | 11/1991 | Drazba et al. | 351/160 |
| 5,100,226 | 3/1992 | Freeman | 351/160 |
| 5,278,592 | 1/1994 | Marie et al. | 351/160 |
| 5,372,504 | 12/1994 | Buechler | 351/47 |

OTHER PUBLICATIONS

Wilson–Ocular Surgery News, Jan. 15, 1994, p. 35.
Colgan–Ocular Surgery News, May 1, 1995, p. 10.
Overmyer–Ophthalmology Times, May 1–7, 1995, p. 14.

*Primary Examiner*—Scott J. Sugarman
*Attorney, Agent, or Firm*—Leonard Bloom

[57] ABSTRACT

Contact lenses with contoured anterior surfaces are employed to obtain informed consent from a patient prior to ophthalmic surgery. These modified contact lenses with contoured surfaces, when worn by a patient, will mimic visual distortions which might result from various types of corneal surgery.

3 Claims, 26 Drawing Sheets

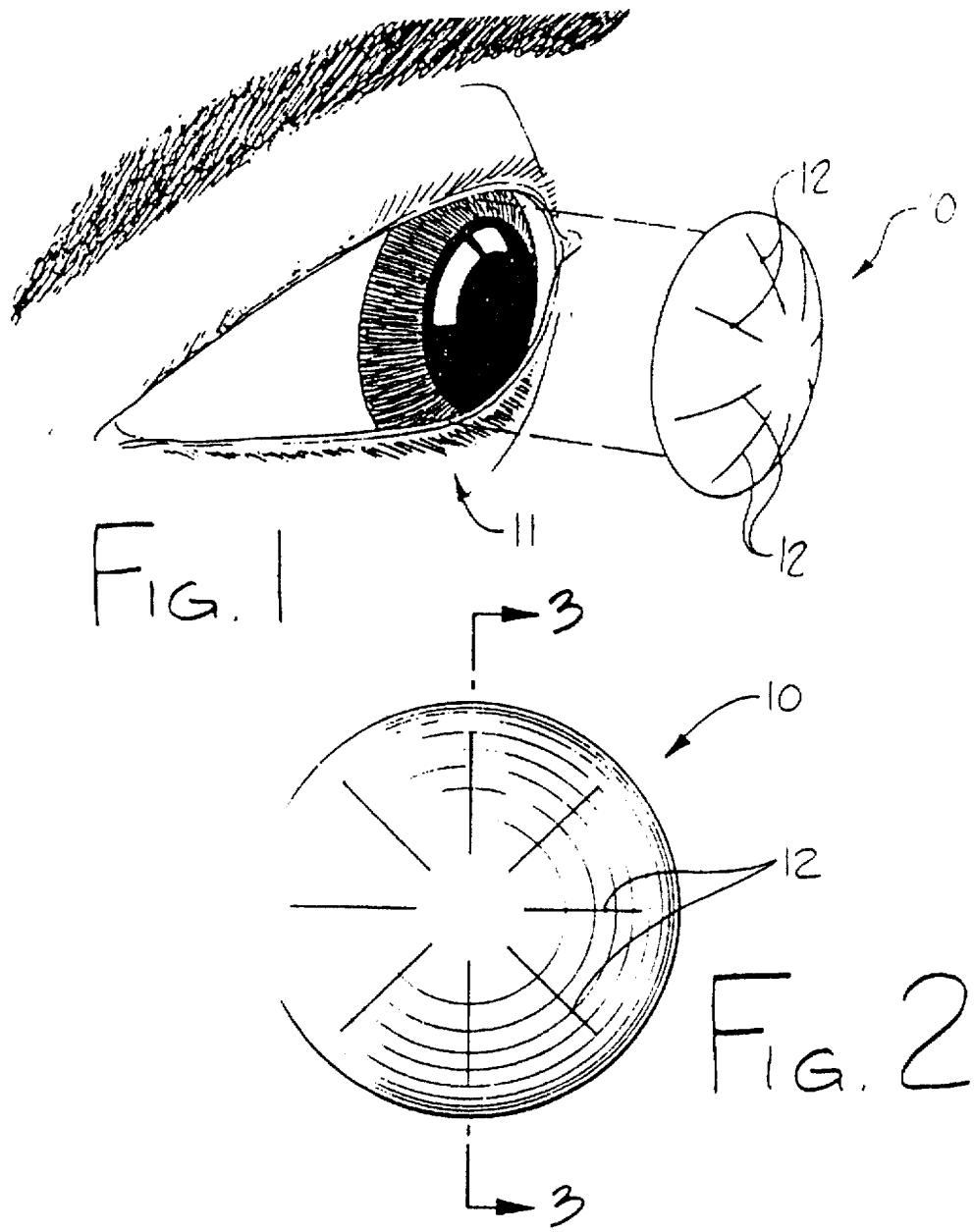

METHOD FOR SIMULATION OF VISUAL DISABILITIES

CROSS REFERENCE TO RELATED APPLICATIONS

This application is a continuation-in-part of our prior application, Ser. No. 331,029, filed Oct. 27, 1994 now U.S. Pat. No. 5,495,305.

STATEMENT REGARDING FEDERALLY SPONSORED RESEARCH OR DEVELOPMENT (Not applicable.)

REFERENCE TO A MICROFICHE APPENDIX SPECIFYING THE TOTAL NUMBER OF MICROFICHE AND TOTAL NUMBER OF FRAMES (Not applicable.)

BACKGROUND OF THE INVENTION

Medical diseases of the eye—as well as eye surgery, such as refractive surgery—can create post-operative visual disturbances for the patient. Because of this post-operative risk of visual disturbance, informed consent from the patient to the doctor is essential. As part of the presently practiced method of informed consent required from the prospective patient prior to surgery, the doctor describes to the patient what visual anomalies to expect as a result of the surgery. This description is open to subjective interpretation by the patient, and in many instances the information conveyed to the patient by the doctor is inadequate and is misinterpreted by the patient.

Significant visual distortions may commonly occur with cataracts and macular degeneration which, respectively, are the leading causes of treatable and non-treatable blindness in the United States. These diseases affect millions of patients and the visual difficulties suffered by the patients are sometimes difficult for medical personnel and the families of patients to understand and to appreciate.

Additionally, new refractive procedures, radial keratotomy (RK) and its related surgery, astigmatic keratotomy (AK) and excimer laser photorefractive keratectomy (PRK), are being performed on growing numbers of patients. Radial keratotomy (RK) and excimer laser photokeratotomy (PRK) are the dominant surgeries for the correction of refractive errors of the eye. It is estimated that approximately 300,000 to 500,000 RK procedures were performed in the U.S., and 250,000 to 300,000 PRK procedures were performed world wide during the year 1993. These surgeries are performed to correct myopia (near-sightedness) and astigmatism. Alone, myopia affects at least thirty percent of the population of the U.S. and higher proportions of the population in Far Eastern countries. PRK is also undergoing clinical trials, and approximately one million myopes will undergo PRK yearly in the U.S. once the procedure is finally approved by the FDA. PRK also shows promise for the correction of hyperopia (farsightedness).

Other refractive procedures are undergoing development which may extend the applicability of refractive surgery. These procedures include intra-lamellar corneal rings, automated lamellar keratectomy (ALK), intrastromal photoablation and "flap and zap" (ALK combined with PRK). All of the foregoing refractive procedures have the potential for reducing visual acuity and/or creating optical aberrations. Obtaining good (and legal) preoperative informed consent from patients undergoing these procedures, especially where there is an increasing amount of advertising relating to such surgery, is necessary and important. This is so because there is potential for postoperative permanent visual degradation from glare and loss of contrast sensitivity. Unmet patient expectations can create disappointment and anger and can lead to malpractice suits, even when good postoperative results are obtained.

SUMMARY OF THE INVENTION

The main purpose of the present invention is to simulate some of the visual problems which may be encountered in refractive surgery (especially, starbursting with RK and glare with PRK). This simulation of visual problems will enhance the level of patient education, and communication between doctor and patient, in obtaining legally sufficient informed consent. Since visual distortions are phenomena that are difficult to explain, the invention provides great benefit to the patient, as well as the doctor, since the patient can be objectively apprised of how the surgery could affect postoperative vision.

The herein disclosed invention provides methods for the patient to effectively assess the result of prospective surgery, so that he or she might have a means of evaluation based on his or her own physiological response.

With all this in mind, the inventors have provided a series of modified contact lenses, which when worn by a patient will produce the type of postoperative visual distortions that could be expected in some cases as a result of surgery of various types of eye surgery. Having worn the lens or lenses, and having actually experienced the visual distortion that could be produced as a result of surgery, the patient can make an educated judgement and give informed consent to the doctor prior to having surgery performed on the eye or eyes. Since the patient has worn the lenses and experienced visual distortion, he or she is less likely to complain to the doctor about any post-operative visual anomaly.

In addition to being useful for providing informed consent, the lenses of this invention also have educational uses. The lenses simulating visual disturbances and disease have significant educational utility for medical students and nurses in the classroom, as well as for doctors in practice. The lenses can be used to educate families of patients with ocular disease regarding the patient's pre-operative visual distortions, as well as possible post-operative visual anomalies; all of this with a specific view of letting the families know what can be expected as a result of surgery. Besides postoperative anomalies, among the disease conditions that may be simulated by the lenses of this invention are the various manifestations of cataracts, corneal opacities, retinal detachments, possibly macular degeneration, as well as hemi- and quadrantanopias.

The basic contact lenses (CL) used in this invention are produced in a seemingly limitless assortment of curvatures and thickness to meet individual prescription fitting requirements. The lenses are made of a variety of materials, such as hydrogels containing varying amounts of water. Lenses with less than 50% water content are considered to be "low water" lenses. The surface characteristics of the lens can vary. Less reactive surfaces are termed "nonionic" and more reactive surfaces are labeled "ionic". To satisfy cosmetic, as well as prescription requirements of patients, lenses are produced in a variety of colors, such as blue, green, brown, etc. The technology for placing markings on contact lenses is known in the art.

The present invention modifies existing contact lenses in a variety of ways to create optical post operative or disease abnormalities. The lens can be modified with lines or areas that are laser marked or etched. The markings can be molded, painted or dyed onto the surface of soft, hard or gas permeable hard contact lenses. Current lens manufacture routinely incorporates either laser engraving or molding of logos and lens parameters into the margins of soft contact lenses. This same technology can be used to make the lens markings on the lenses of this invention. Soft contact lenses are also frequently painted with opaque colors or transparent dyes to simulate various eye colors. These techniques may be employed to affect the light coming through the contact lens(es) and to create various optical characteristics. More specifically;

1. The glare and nocturnal starbursting experienced in RK may be created with six or eight radial laser marks that extend slightly within the pupillary margin. Small optical zones are frequently employed in RK (2.75 mm) and similar specifications may be used in the current invention. (See drawings)
2. The glare experienced with PRK may be simulated by a slight hazing of the central, 3 to 6 mm of the contact lens.
3. Macular degeneration and cataracts may be simulated by darker or more intense central (optical zone) alteration of the contact lens.

The simplest embodiment of this invention will be based upon using soft contact lenses ("SCL's"), although hard contact lenses ("HCL's"), rigid gas permeable contact lenses ("RGP's"), silicone lenses and hybrid lenses (RGP center and SCL surround, as in the Saturn lenses) may be used. The lenses can be manufactured in any refractive power to fit the patient's individual refractive need and the degree of optical-simulating modification can be titrated with the amount of optical correction (e.g. higher power RK simulating lenses would have more central radial lines, and higher power PRK lenses would have more central haze). A possible embodiment would be an ultrathin lens (such as the CSI-T™) with no optical power (plano) over which the patient could wear his/her contact lenses piggyback style. Soft contact lenses could be provided as disposable lenses.

Macular degeneration would be capable of simulation with a zone of near total opacity (nearly 0% transmission) that would be slightly smaller than the person's pupil. As is well known, pupil size varies with age and is larger at younger age. Pupil size may be 5 to 8 mm in a younger person and 2 to 3 mm in older individuals. The proper size of the central opacity in the contact lens (CL) would be about 4 mm for patients in their twenties or thirties.

It should be possible to simulate visual fields defects from neuro-ophthalmic conditions of the visual pathways such as:

1. optic neuropathies (central scotoma (blind spot) or altitudinal defect (half of the vision obscured above or below a central horizontal meridian through fixation);
2. hemianopia (half of the vision obscured in both eyes together along a vertical meridian through fixation) either homonymous (same side in both eyes) or heteronomous (opposite sides for both eyes—either bitemporal or binasal).

Central scotomas would be simulated by an absolute central CL opacity just smaller than the pupil and field defects would be simulated by opacity covering a half or a quarter of the CL extending through the center of the CL and covering a significant area of the lens (larger than the pupil to perhaps the size of the cornea, 11 to 12 mm). Optically, one may find that central opacities that are larger than the pupil may still allow light to enter the eye as peripheral light rays striking the cornea are refracted toward the pupil by the convex surface of the cornea. Specified opacity and size of opacity relative to the pupil size may require some experimentation to determine the optimum lens modification and therefore need some leeway until actual CL(s) are manufactured and tried clinically on the patient. As a specific modification the opaque CL areas may be oriented by using CL(s) that are toric or are truncated or have a configuration that provides ballast.

As a special embodiment of this invention, eyeglasses (spectacles) are modified so that their lenses are constructed so as to have modifications similar to the modifications on the contact lenses.

An important embodiment of the present invention is a disposable soft contact lens with laser or molded marks. The lens may be made very thin to be worn under (or over) the patient's own contact lenses (piggy back style) or under the patient's eyeglasses. In a preferred embodiment of this invention, the patient's prescription contact lens may be used to make the etched or marked lens.

In its broadest aspect, this invention involves a contact lens useful for simulating an ophthalmologic anomaly (as exemplified throughout this specification) which may be the postoperative result of surgery, comprising a lens whose field of vision has been modified to simulate said ophthalmologic anomaly. Said contract lens can be one whose light transmission has been modified to produce the glare and nocturnal starbursting experienced in radial keratotomy. The glare and nocturnal starbursting can be produced by four, six or eight radial marks that extend slightly within the pupillary margin.

As an alternative embodiment, the light transmission of the contact lens has been modified to produce the glare experienced after photorefractive keratectomy. In this embodiment the glare can be produced by a slight hazing of the central portion of the contact lens. In another embodiment the hazing is of 3 to 6 mm of the central portion of the contact lens.

The invention herein described is most concerned with a method for obtaining informed consent from a patient prior to surgery by fitting the patient with a device, the field of vision of which has been modified to simulate the ophthalmologic anomaly which might be experienced by the patient as a result of said surgery. The modified device can be a contact lens, an eyeglass or a pair of eyeglasses.

An important method of obtaining informed consent from a patient prior to surgery comprises fitting the patient with a virtual reality device which has been programmed to simulate the ophthalmologic anomaly which might be experienced by the patient as a result of said surgery, and then obtaining informed consent.

A significant cause of glare after refractive surgery Radial Keratotomy (RK), Photorefractive Keratotomy (PRK), Laser Assisted Institu Keratotomy (LASIK), etc. come from an irregular anterior corneal surface created by the refractive surgery (anterior irregular astigmatism). This affect may be more important than the opacities (stromal scarring or radial scar spokes) caused by the surgery and spherical variations in the optical zone. This anterior irregular astigmatism causes glare, reduced best corrected (and uncorrected) visual acuity and halos at night. The following helps better describe the anterior irregular astigmatism and effects of optical zone in context of post-surgical corneal topography and proposes a more specific group of surface contoured contact lens embodiments for simulating the problems related to refractive surgery.

The contoured surface of the lenses of this invention can be produced by molding, etching or cutting; and they can mimic four incision radial keratotomy, two incision astigmatic keratotomy, T-cut, paired "T-cuts", arcuate cuts and paired arcuate cuts.

It is important to bear in mind that the contoured anterior surface of the lens is designed to mimic the post-operative contour of the cornea. This is generally at present up to 6 mm diameter and a depth of 50–100μ, and generally 50–100μ. The actual dimensions may vary based on the refractive index of the material (e.g. plastic, polymer, or glass) used for the contact lens.

It is to be noted that the surface markings as well as contours could be made by stick-on transparencies onto the surface of the contact lens.

BRIEF DESCRIPTION OF THE DRAWINGS

FIG. 1 is a perspective view of the contact lens of this invention about to be fitted into the eye. The contact lens having eight radial lines.

FIG. 2 is a front elevational view thereof.

DESCRIPTION OF THE PREFERRED EMBODIMENTS

With reference to FIG. 1, a contact lens 10 of this invention about to be fitted into the eye 11 has eight radial lines 12. The contact lens 10 with radial liens 12 when worn will simulate glare and nocturnal starbursting, a visual anomaly which may result from radial keratotomy (RK).

Figure 3:
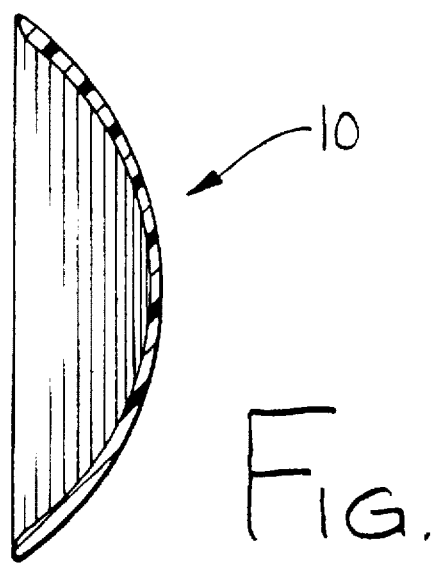
FIG. 3 is a cross-sectional view taken along lines 3—3 of FIG. 2.

The contact lens 10 can be a conventional contact lens 10 (FIGS. 2 and 3) which has had its field of vision modified by etching, dying, etc. to form the lines 12 or other contemplated configurations (FIG. 2).

Figure 4:
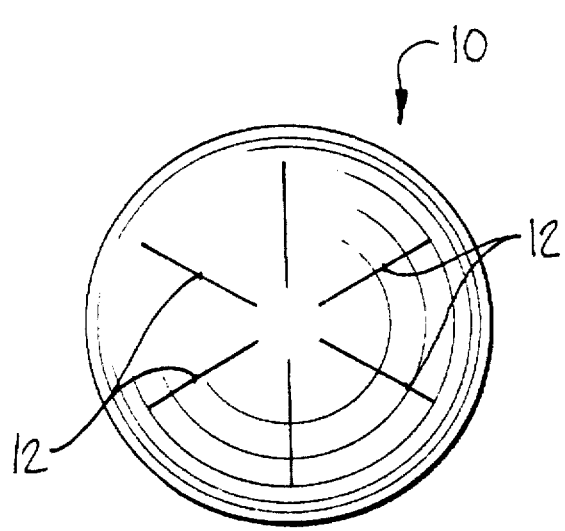
FIG. 4 is a front elevational view of the contact lens with six radial liens.
Figure 5:
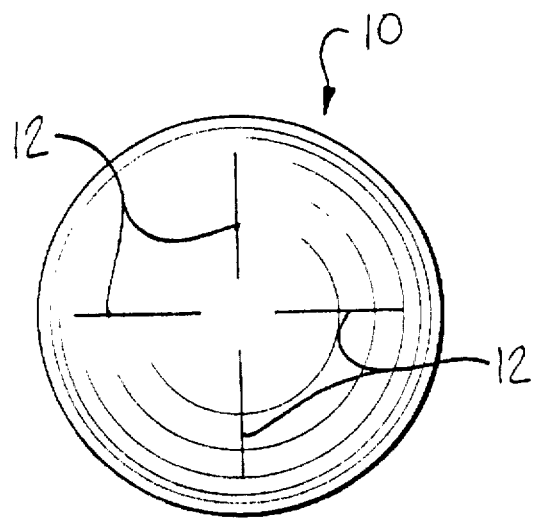
FIG. 5 is a front elevational view of the contact lens with four radial lines.

The contact lens 10 to simulate glare and nocturnal starbursting may have a varying number of radial lines 12. FIGS. 2, 4 and 5 are examples of lenses 10 with radial lines 12 producing varying degrees of glare and nocturnal starbursting.

In the case of RK, the visual effects of the lenses 10 are created by making radial lines 12 on or in the lenses 10 in the same patterns that are incised into the cornea in performing RK. Four, six or eight radial lines 12 would be made with optical zones of 1.75 to 5.0 mm (RK optical zone range) extending toward the rim of the lens to a diameter of from 10 to 12 mm. The lines 12 would be 0.1to 1.0 mm wide and white in color. The lines would most ideally be laser etched onto the soft contact lens (SCL) or the lines could be fine ridges or depressions molded into the lens when manufactured. Opacity could be created by molding fine cross hatching, dimples or parallel lines in the same dimensions used by lens manufacturers when imprinting SCLs with parameter and brand logo indicators. Height or depth of molded lines are in the tenths of mm. Hatching, etc. would be in the hundredth to tenths of mm (ex. illustration of B&L disposable lens). Alternatively, various lines and patterns can be painted on the surface of the lens (like in opaque colored cosmetic contacts) or dyed onto the lens or created with a photo engraving process. Ideally, the lines 12 should extend through the substance (e.g., plastic) of the CL to give some of the depth such as actual RK scars exhibit. Actual scars are 100% of the corneal thickness as measured in the para central zone by ultrasound contact pachymetry (0.500 mm+/−0.100 mm).

Figure 6:
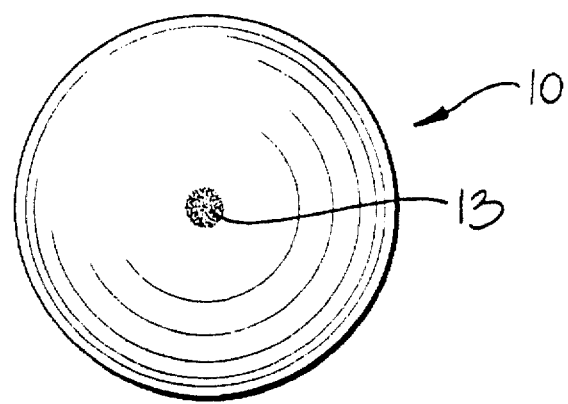
FIG. 6 is a front elevational view of the contact lens with slight hazing.

The glare which may be experienced after photorefractive keratectomy (PRK) may be simulated by a slight hazing 13 of the central 3 to 6 mm of the contact lens 1 (FIG. 6).

In the case of PRK, the central cornea is ablated with an excimer laser in an optical zone of 6.0 mm+/−2 mm to achieve a central flattening to correct myopia. As the cornea heals, this area may develop a fine reticular haze that may take several months to fade and may be permanent. This haze gives a glare, slight blur or a loss of contrast sensitivity. The effect of the haze is most prominent at night when bright oncoming lights may give a glary "dirty windshield" effect. To simulate the optical aberrations of PRK the 6.0 +/−2 mm optical zone of the SCL would be modified to create a fine hazy pattern similar to that of a healing cornea. Actual photographic examples of clinical haze may be used as models to determine the degree of opacity. The front surface of the contact lens may be modified to create the anterior irregular astigmatism that develops as the cornea epithelium heals and the regeneration of new stromal collagen occurs. Central corneal islands (irregular areas of ablation) may be simulated by the contact lens, as well. If there are measurements or units of light scatter used in physical optics, the required amount or degree would be mild in the case of PRK modeling (as compared to say cataracts where significant scatter/opacity would be indicated). Techniques similar to those used for the RK SCL could be employed e.g., molding, laser etching, dying, painting or photographic processes.

Figure 7:
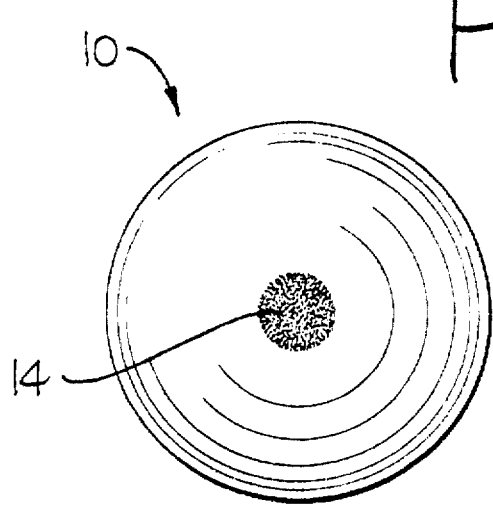
FIG. 7 is a front elevational view of the contact lens with moderate hazing.
Figure 8:
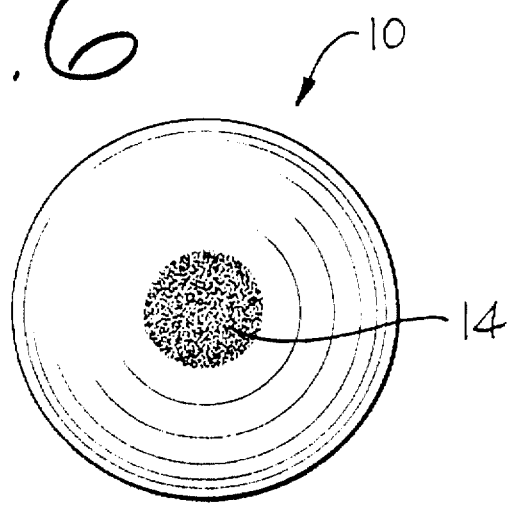
FIG. 8 is a front elevational view of the contact lens with substantial hazing.

Macular degeneration and cataracts may be simulated by darker or more intense central (optical zone) hazing 14 of the contact lens 10 (FIGS. 7–8).

Figure 9:
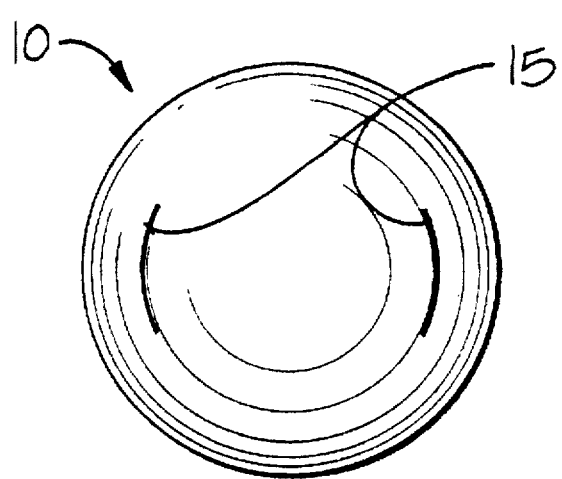
FIG. 9 is a front elevational view of the contact lens with paired arcuate cuts.
Figure 10:
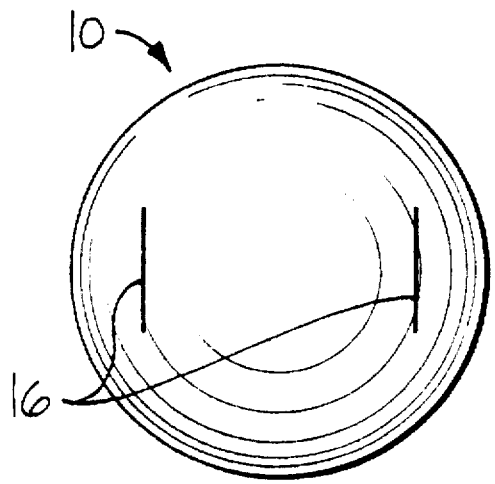
FIG. 10 is a front elevational view of the contact lens with paired "T-cuts".

With reference to FIG. 9 a lens 10 with paired arcuate cuts 15 approximately 6 mm apart; and with reference to FIG. 10 paired "T-cuts" 16 approximately 6 mm apart. The lenses of FIGS. 9 and 10 are of a size to cover the cornea. Arcuate 15 or T-cuts 16 for AK could be simulated (astigmatic cuts), although these cuts would probably be less useful since they would be as pairs 180 degrees apart, at a 6 mm optical zone (and 30 to 90 degree extent), and may be far enough away from the optical zone that they would not create much visual effect.

Other medial opacities, such as corneal scars, corneal edema or cataract, could be simulated by creating central optical zone haze 14 or opacity of denser magnitude to decrease light transmission and increase light scatter. [Scatter effects would be more important than reducing light transmission; as sun glasses that have only 50% or 10% transmission may allow persons with normal vision to still see satisfactorily.] Sufficient haze to reduce vision to say 20/50 or 20/60 would demonstrate moderate clinically significant disease and reductions to 20/200 or 20/400 would demonstrate advanced opacities. Wedge-shaped clefts, variable opacity and brown discoloration in the lenses would produce an effect similar to actual cataracts.

Figure 11:
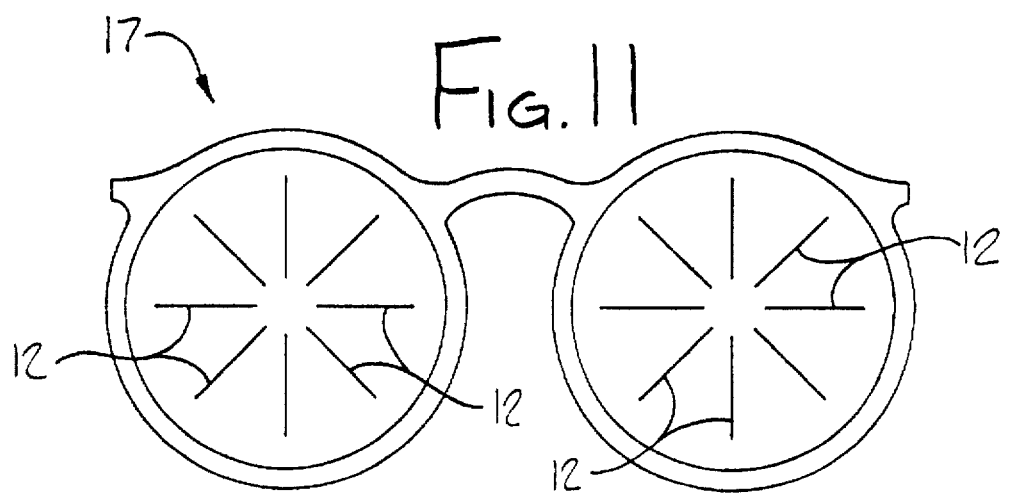
FIG. 11 is an elevational view of eyeglasses with lenses marked with radial lines.
Figure 12:
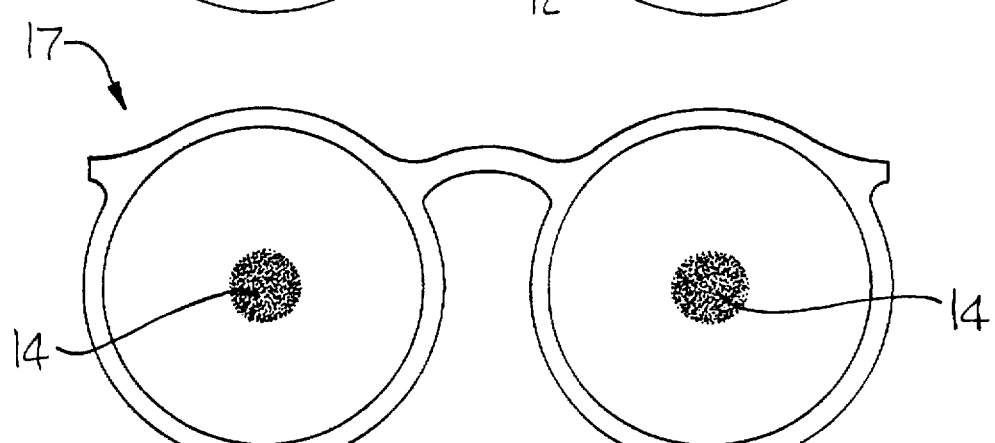
FIG. 12 is an elevational view of eyeglasses with central hazing.

There are times when the patient will not be able to wear contact lenses. With this being the case this invention supplies eyeglasses 17 with various markings simulating visual anomalies (FIGS. 11–12). FIG. 11 simulates starbursting and the hazing 12, and FIG. 12 simulates glare 14 which may be experienced after RK and PRK, respectively.

Figure 13:
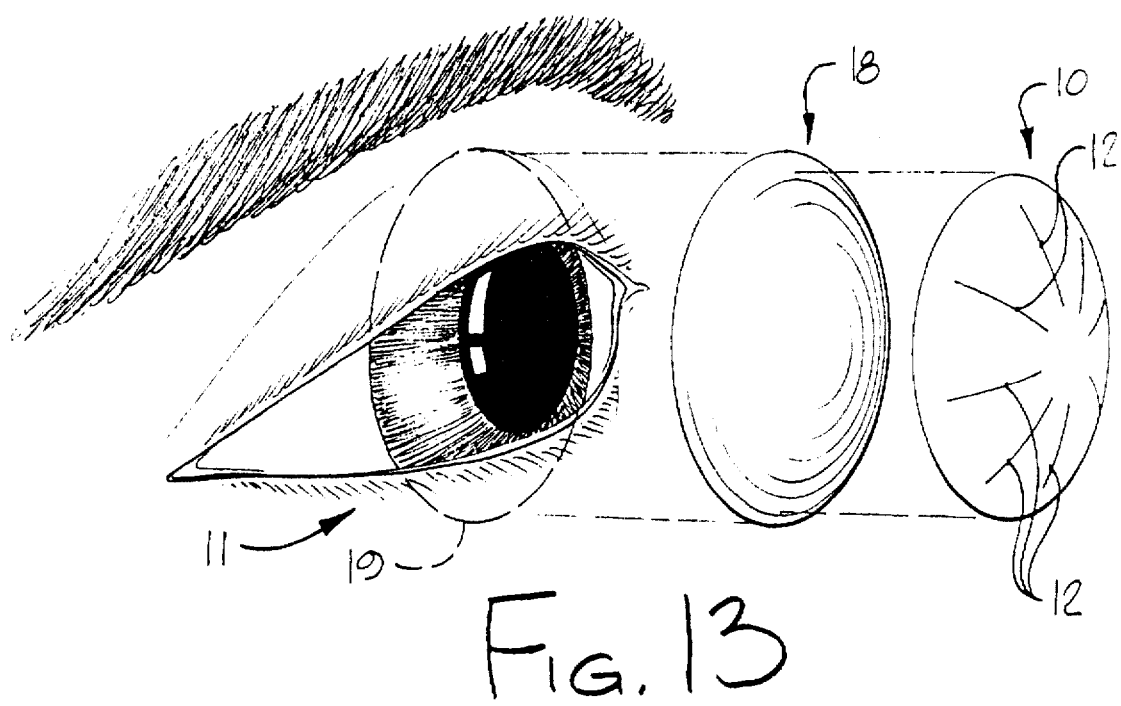
FIGS. 13 and 14 are views illustrating contact lenses of this invention worn piggyback, one lens over the other.
Figure 14:
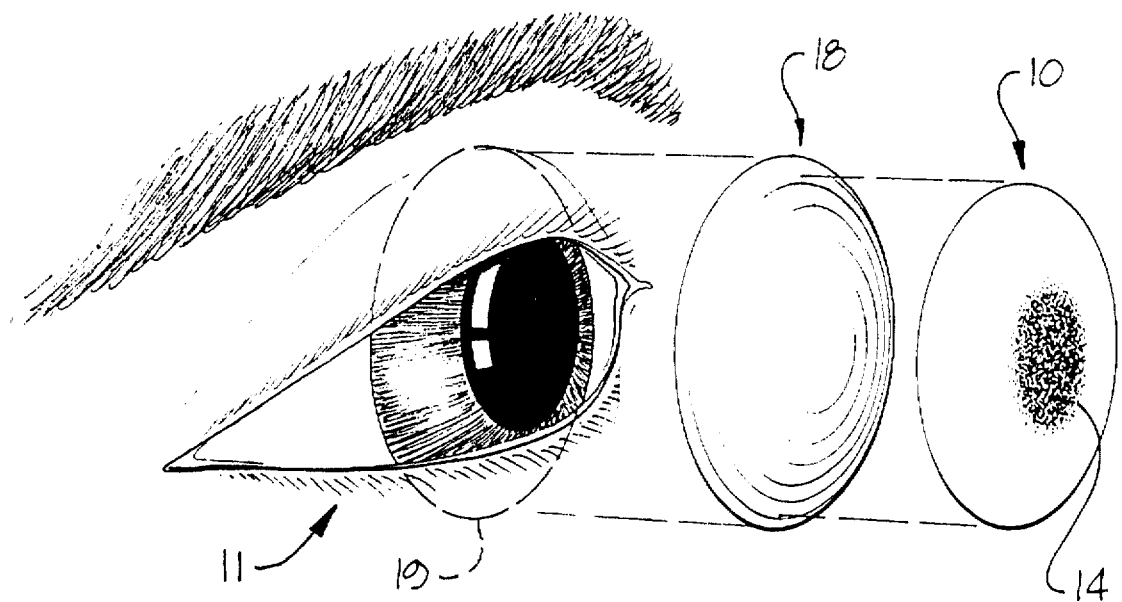

The contact lenses of the invention would be worn piggyback (FIGS. 13 and 14). That is the contact lens with the altered field of vision could be worn over the patient's prescription contact lens (FIGS. 13 and 14).

Figure 15:
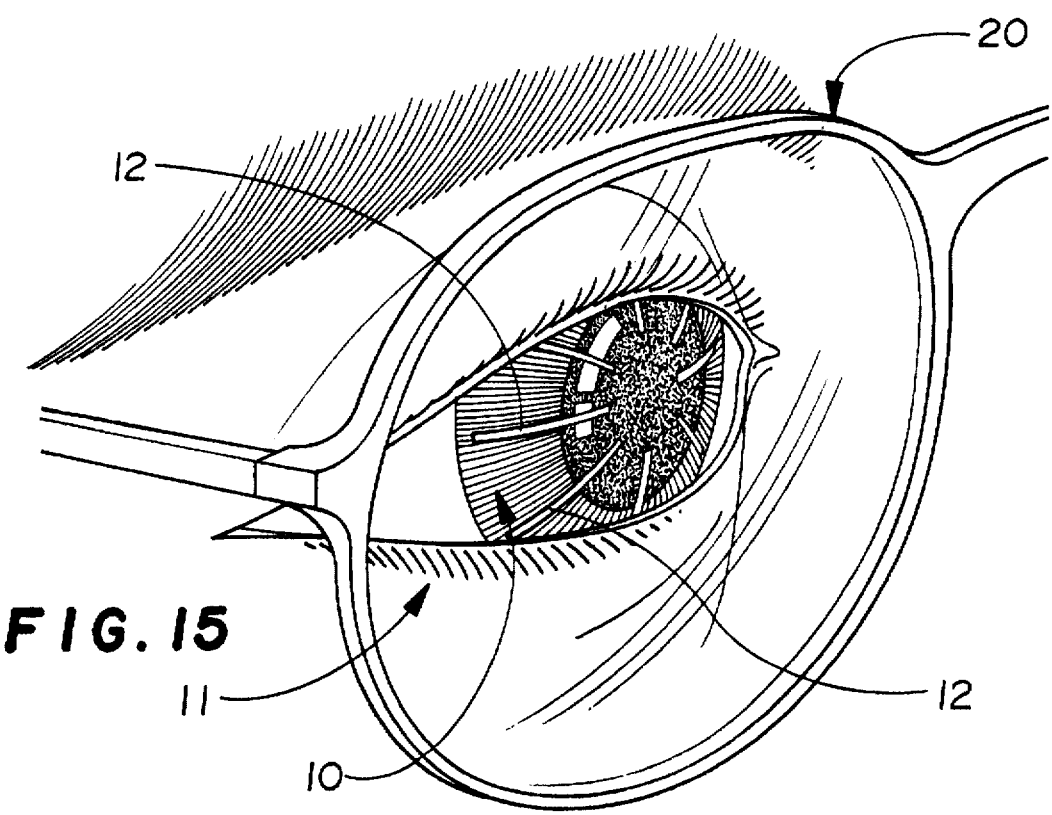
FIG. 15 is a view illustrating contact lenses of this invention worn under eyeglasses. The eyeglasses are only partially shown for ease of illustration.

With reference to FIG. 13 the contact lens of this invention 10 with radial lines 12 is worn over the patient's prescription contact lens 18, and in FIG. 14 the contact lens 10 with hazing 14 is worn over the patient's prescription contact lens 18. The dashed lines 19 in FIGS. 13 and 14 represent the area of placement of the contact lenses 10 and 18 in the eye 11. The contact lens 10 besides being worn in conjunction with prescription contact lenses 18, can be worn along with a patient's prescription eyeglasses 20 (FIG. 15). With the contact lens 10 worn piggyback over the patient's prescription CL 18, or in conjunction with prescription eyeglasses 20, the patient will be able to attain a more accurate assessment of possible visual aberrations prior to surgery and thereby give more meaningful informed consent.

Additional embodiments of this invention are possible as further exemplified.

The size of the optical zone can cause visual problems. A small optical zone may create halos, especially at night when the pupil may dilate to be larger than the optical zone. This problem is frequently seen with excimer PRK when used to correct higher degrees of myopia. This type of distortion may be simulated by limiting the optical zone of the contact lens to the maximum possible with PRK (approximately 6 mm with current technology). The 6 mm optical zone may be a blend with only the center of the zone (3 or 4 mm) possessing the full optical power required.

The accuracy of RK and PRK optical correction is limited. Some patients will have uncorrected vision of 20/20; however, some will have vision of 20/40. (Based on most studies for corrections of up to −6.00 diopters.) This is in part due to over and under corrections. Under corrections may be simulated by having a degree of residual myopia, perhaps −0.50 to −0.75 diopters from the ideal correction; e.g. too weak a contact lens correction. Conversely, over corrections can be simulated by too strong a contact lens. These over and under corrections may be achieved by selecting a CL with slightly greater or lesser power than ideal or by having a small degree of plus or minus correction in a piggyback CL. An over correction of a myope would correct too much myopic or minus power, adding too much plus or hyperopic power, thus leaving the patient net plus.

Astigmatic correction deficiencies may be simulated with lenses that do not fully correct the astigmatism.

Each of the types of CL simulation may be used singly or in combination, either in a single CL or in a set of CL's.

A noteworthy embodiment of this invention envisions a set of modified contact lenses of this invention supplied in a kit. Lenses with radial lines, hazing, etc. would be included in the kit. The kit with the lenses would be convenient for supplying the doctor with contact lenses and could be supplied and used as an educational tool in the classroom. The kit and/or lenses may be disposable.

It is obvious to those skilled in the art that lenses with modified fields of vision simulating visual anomalies could be incorporated into a phoropter or trial lens set. The doctor could use such a device for obtaining informed consent from a patient.

Figure 16:
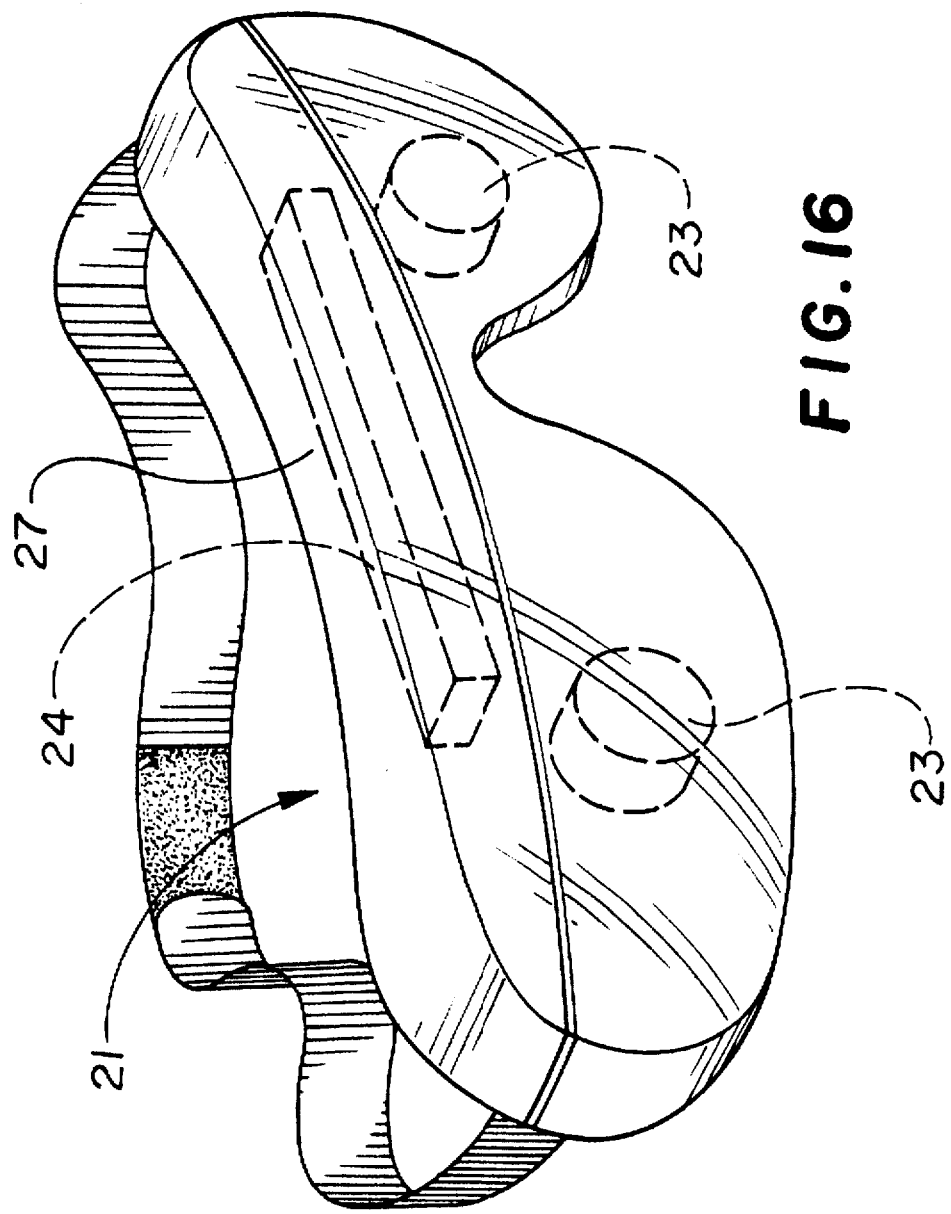
FIG. 16 is a front perspective view illustrating a pair of Virtual Reality Goggles.
Figure 17:
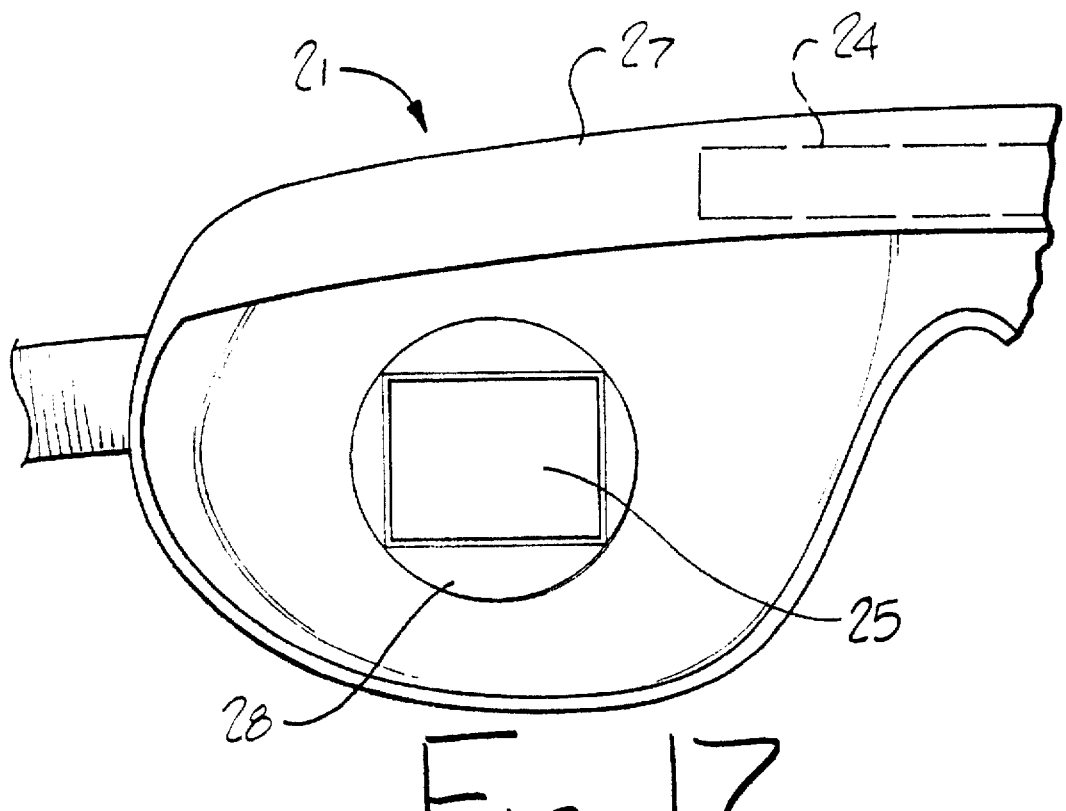
FIG. 17 is a rear elevational view thereof with part of the goggles broken away for ease of illustration.
Figure 18:
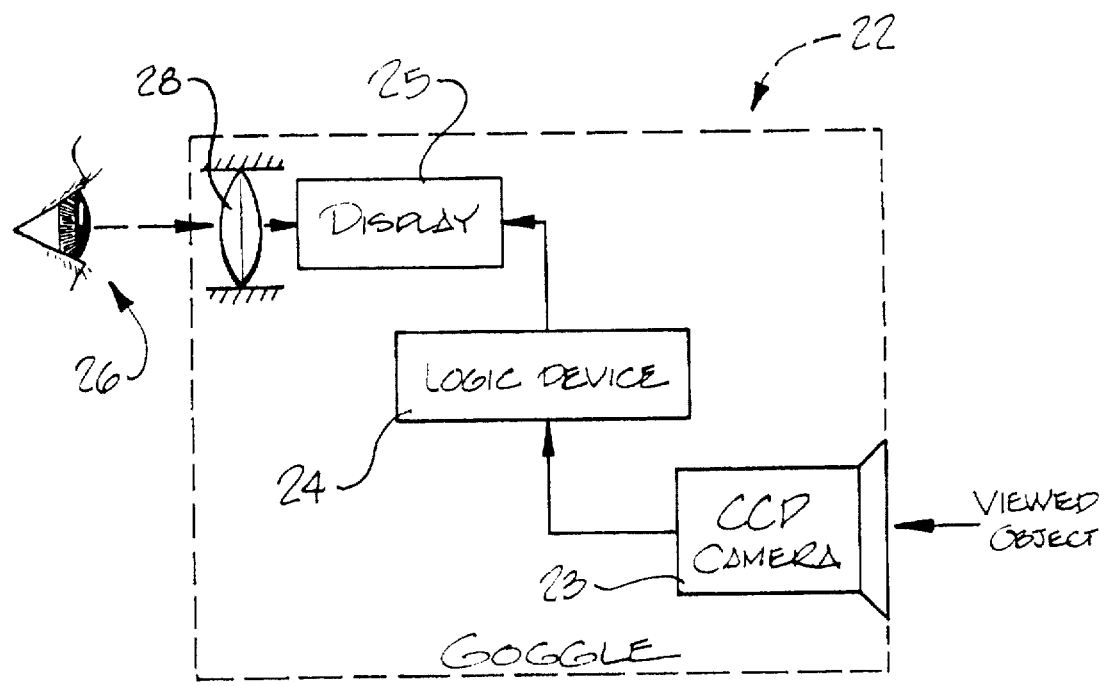
FIG. 18 is a block diagram representing the methodology employed in using Virtual Reality Goggles.

As a special and unique embodiment of this invention T.V. and computer programs technology can be used to simulate visual disabilities described herein (FIGS. 16-18). Virtual Reality Goggles 22 (block diagram FIG. 18) may be constructed so that real time images from a T.V. camera (CCD) 23 are processed through software (logic device) 24 that creates the above described visual distortions which are displayed 25 in the goggles 22. In this embodiment the patient 26 would wear a virtual reality device or Virtual Reality Goggles 22 and the doctor would insert the program which would display on a T.V. screen in the goggles 25 the visual anomaly that could be expected as a result of the contemplated surgery. The Virtual Reality Goggles 22 are constructed so that real-time images from a T.V. camera (CCD) 23 are processed through software that creates the above described distortions which are displayed in the goggles 22.

The top of the glasses 27 houses the logic device 24. The eye piece of the glasses houses a small TV camera (CCD) similar to that used in children's video games ("Sega" T.M. style Virtual Reality Goggles). On the inside of the goggles there is a convex lens 28 to focus the image.

With reference specifically to the block diagram (FIG. 18) the patient 26 views the image through the convex lens 28 to focus on the display 25. The logic device 24 distorts the vision according to an algorithm for glare-loss of focus. The CCD 23 camera focuses on the viewed object.

With the use of Virtual Reality Goggles the doctor has an added dimension for obtaining consent from the patient.

Many advantages are envisioned by the use of the contact lenses of this invention. Primarily, the contact lenses when worn by the patient will simulate visual distortions that might be experienced postoperatively. Thus the informed consent from the patient after wearing the contact lenses will be more meaningful. This is so because the consent will be based on information derived from an objective physiological assessment, rather than a subjective verbal communication between doctor and patient. The use of contact lenses simulating postoperative visual defects may become the standard for legal informed consent in ophthalmologic surgery. Aside from being instructive to the patient, the contact lenses herein described are an educational aid. Student doctors, nurses and other interested parties, such as members of the family of a candidate for eye surgery could apply the contact lenses to objectively apprise themselves of possible postoperative visual deficiencies.

With reference to the figures, the contact lenses of this invention are designed to produce visual distortions which might result from excimer photo refractive keratotomy (PRK), as well as radial keratotomy (RK). The figures are not drawn to scale.

Figure 19:
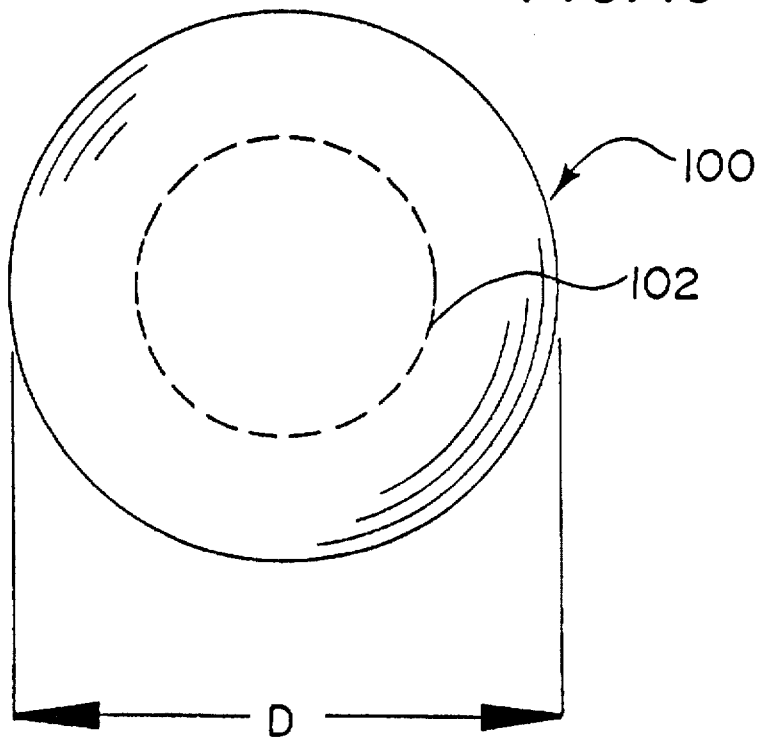
FIG. 19 is a front view of a contact lens with the dashed lines indicating the optical zone.

Regarding FIG. 19, a soft contact lens 100 describes a 6 mm optical zone 102 which is the maximum size approved at this time for photo refractive keratotomy (PRK). The diameter (D) of the lens in practice is 11-15 mm with the most conventional diameter being 13.8 to 14.5 mm. Base curves usually run from 8 to 9 mm. Hard or rigid gas permeable lenses are large of about 6 to 10 mm; soft lenses would be the preferred embodiment of the present invention.

Photorefractive keratotomy (PRK) is an evolving art, and while at present with laser surgery the maximum diameter of ablation is 6 mm, some laser companies are producing lasers creating a 9 to 9.5 mm optical zone. Multiple optical zones, e.g. three may be cut thereby creating an aspheric cut to blend peripheral treatment zones and thereby decrease needed depth of treatment. However, halos would still be a problem. While the optical treatment zone of 6 mm is approved at this time, the zone may increase to 7 mm with Visx™ or larger with Nidek™ or other later generation lasers. This size of 7 to 8 mm should be large enough to overcome most optical zone halo problems. However, the optical zone size may be limited if the depth of treatment would be too great.

Figure 20:
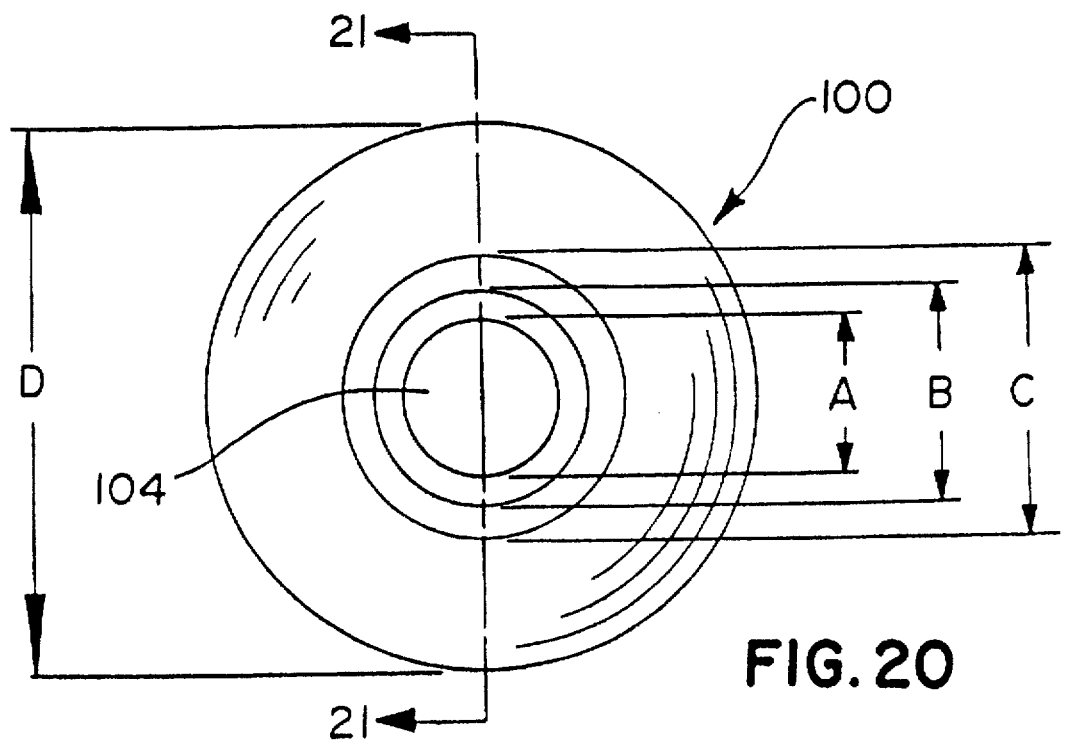
FIG. 20 is a front view of a contact lens with the center circles indicating the dimensions of the ablated areas.
Figure 21:
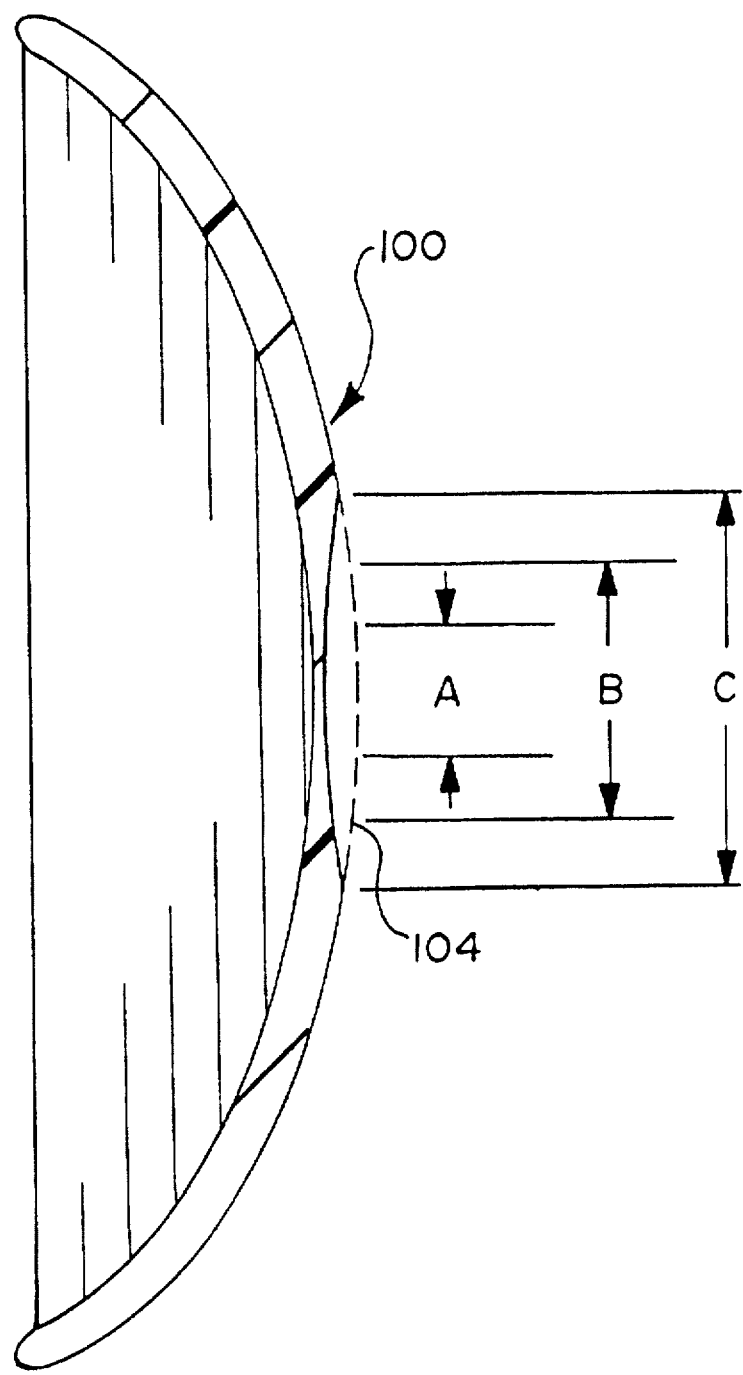
FIG. 21 is a cross-section taken along 21—21 of FIG. 20.

Excimer photo refractive keratotomy (PRK) removes tissue, flattening the cornea in the zone of treatment. The contour of flattening may be spherical or aspherical. Surgery by photo refractive keratotomy is usually performed with one to three zones of ablation with each zone producing a different degree of flattening (FIGS. 20 and 21). The outer zones have less power, creating an aspherical flattening. Multizone ablation is done to blend the transition into the untreated cornea for better healing and to diminish the required depth of ablation. Thus a multifocal cornea is created, with the possibility of producing glare and blur depending on the size of the ablated optical zone in relation to the size of the pupil.

Ablation 104 of the lens 100 shown in FIGS. 20 and 21 mimics the ablation that results from PRK. The arrow D represents the diameter of the lens. Arrows A, B, and C represent a three zone ablation 104 of the optical zone of the contact lens, with arrows A, B, and C represent 4 mm, 5 mm, and 6 mm optical zones respectively. Outer zone C of 7-8 mm and as high as 9-9.5 mm are possible. Zone A of approximately 3 to 5 mm and B of 4 to 6 mm are conventional for the inner and intermediate zones in a three zone ablation. The modification involves modifying the anterior surface of contact lenses to mimic the surface contour or topography of the cornea after ophthalmic surgery. In the contact lens of FIG. 21 the back curvature is usually 8 to 9 mm. Regular contact lenses provide a large enough optical zone to prevent glare or halos. The optical zone or blend of optical zones, usually three optical zones for higher degrees of myopia may be a cause of halos or glare—especially at night when the pupil may dilate to a size nearly that or even greater than that of the optical zone.

The healing response may influence the shape of the cornea in ways that are not predictable on a case by case basis. Moreover, the healing process, after surgery generally tends to fill in the cornea with new collagen, reversing some of the effects of the surgery. This healing may result in an irregular front surface of the cornea, producing, at times, visual distortion.

Inhomogeneity of the laser beam profile may result in areas of the cornea that are not evenly treated.

A preferred embodiment of the present invention, in addition to simulating with a contact lens the opacities or haze induced by refractive surgeries, may also more importantly simulate the various aforementioned changes in the anterior (refracting) corneal surface. These variations in the topography of the cornea, intentional or unintentional, significantly affect the quality of vision. By duplicating these corneal surface changes in a contact lens, the patient can better experience what "visual life" may be like post operatively in various lighting, recreational and occupational environments, and will be able to give the surgeon more adequate informed consent prior to surgery.

In the preferred embodiments of the invention, the contact lens resembles in contour the post operative changes of the cornea. Among the contours are the following: In RK patients there is a variation in surface contour wherein the central cornea is flattened over a 2 to 5 mm area of the optical zone. The periphery of the cornea is steepened. Since the periphery is not of uniform contour, areas over the incisions are flatter than areas between the incisions (by a fraction of a diopter to perhaps 3 to 4 diopters). This complex refractive surface shape leads to optical aberrations, especially nocturnal halos, glare, and loss of best corrected visual acuity or contrast sensitivity. This optical effect, is in addition to the diffraction or glare effects of the radial lines.

Figure 22:
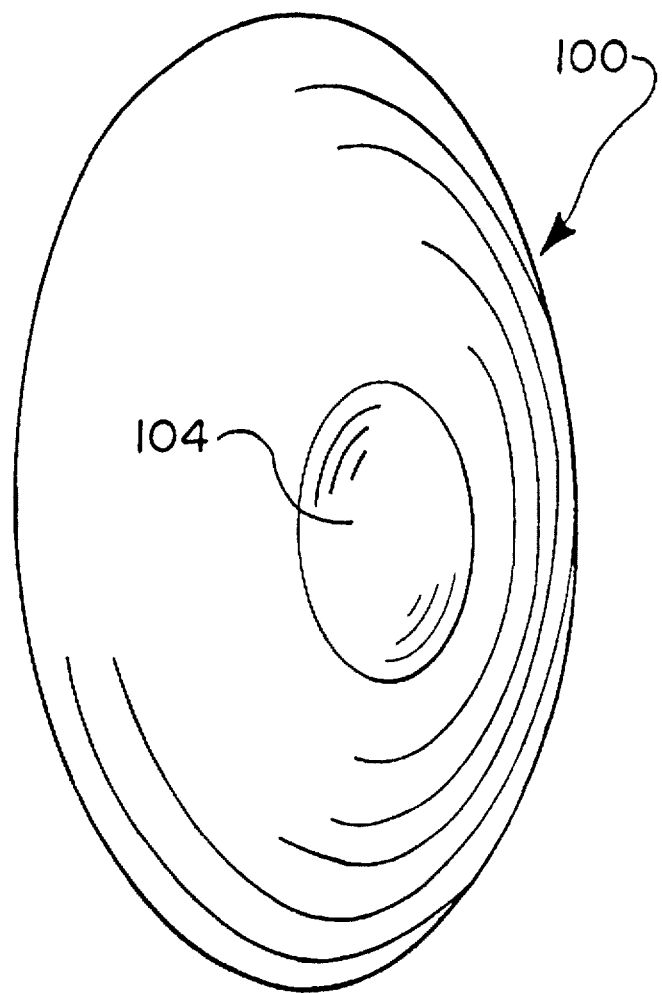
FIG. 22 is a perspective view of a contact lens showing an ablated area.
Figure 37:
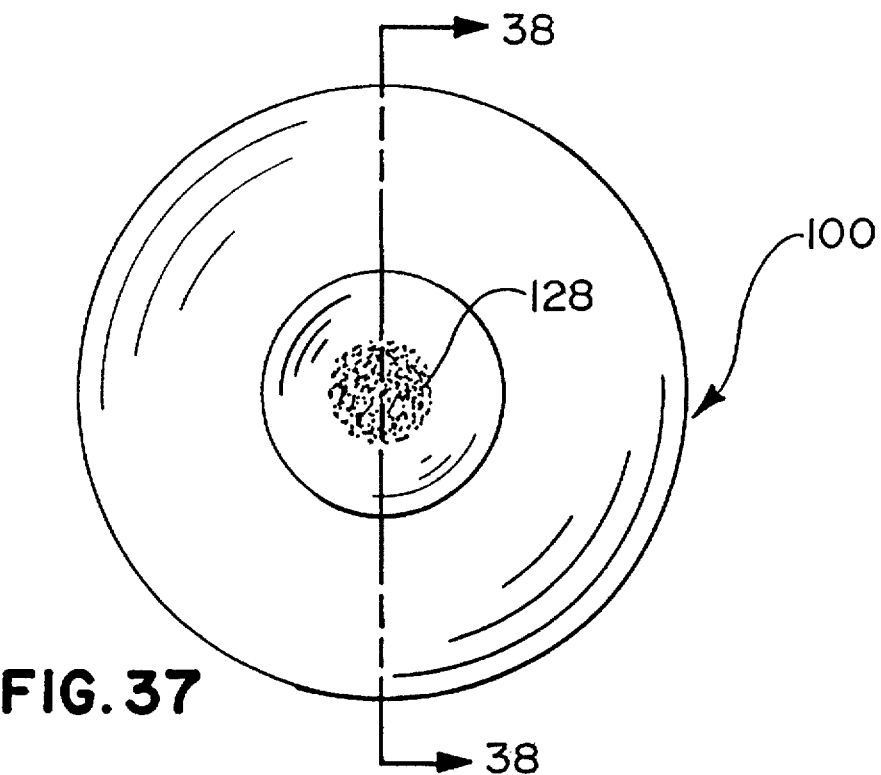
FIG. 37 is a view of a contact lens illustrating haze on the posterior surface, with ablation on the anterior surface.
Figure 38:
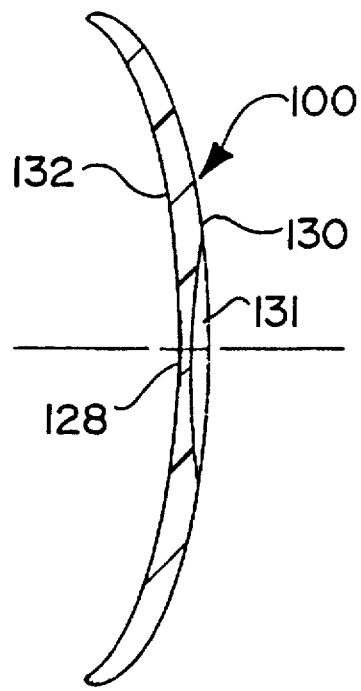
FIG. 38 is a section taken along lines 38—38 of FIG. 37.

The contact lenses for simulation of excimer laser PRK (FIGS. 21–22) is an important embodiment of this invention. The lens 100 of FIGS. 21–22 illustrates an ablated area 104 of the contact lens which will mimic the area of the cornea which was ablated during PRK surgery. In addition to haze (FIG. 37), central islands (FIGS. 26–28) and optical zone size effects, as well as inadvertent decentration of the optical zone (FIGS. 23–25) by the surgeon will be a most likely source of complaints of halos, glare, and vision loss. Clinically significant decentration would be from about 0.5 to 2 mm from alignment with the pupil or the visual axis.

Creating a set of lenses to perfectly match each individual's actual degree of myopic or astigmatic correction and possible degrees of haze to give the patient an exact idea of likely optical changes would require an unwieldy, large set of contact lenses. However, an elegant solution to the problem of the unwieldy set of contact lenses is obtained if a blank lens is provided that can be lasered by the actual excimer laser that is to be used to treat the patient. This lasering is easy to do with hard contact lenses since the calibration of the laser is checked by lasering plastic lenses having the patient's prescription. To do this same lasering process with a soft contact lens, requires a holder for the lens support, since soft contact lenses (SCLs) are flimsy. The lens holder has a spherical contour like the cornea, with a peripheral flange to keep the lens in place. The bottom of the holder would be flat or round to allow orientation with a brace. Such braces are known in the art and are currently used for laser instruction. In such instruction, a Styrofoam face-mask simulating the patient's face is oriented under the laser. The mask is molded with depressions where animal eyes are to be placed for practice ablation. In real practice, pre-made soft contact lenses would likely be used in lieu of custom lasered lens.

The following figures portray the anterior contour of a contact lens relative to the topography of the post surgical cornea. The preferred contact lens for the simulation of visual disability after PRK, simulates the post operation (p.o.) surface of the eye after ablation, simply specifying a particular optical zone and a mild degree of haze. Anterior irregular astigmatism from irregular or decentered ablation and areas like central islands or irregularly layered or healed epithelium could be simulated for the patient to experience other potential post operative problem affects.

Figure 23:
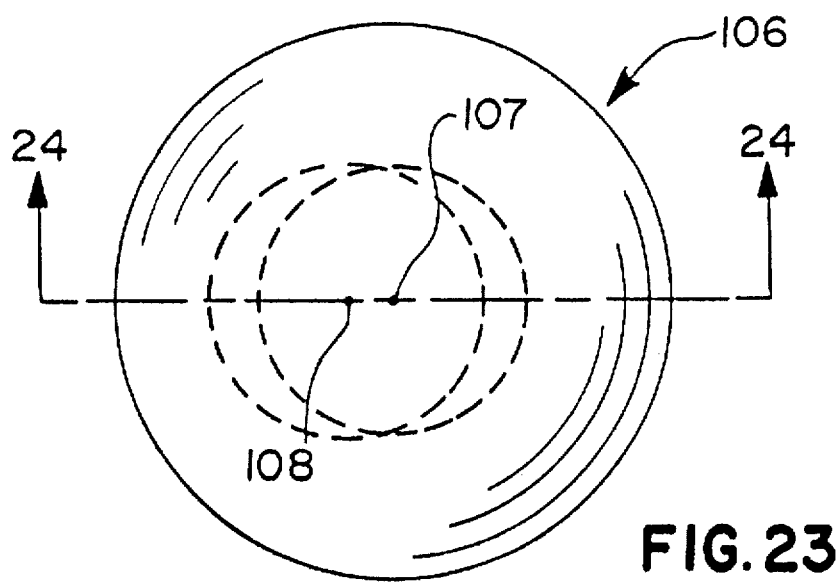
FIG. 23 is a front view of a contact lens illustrating decentered ablation.
Figure 24:
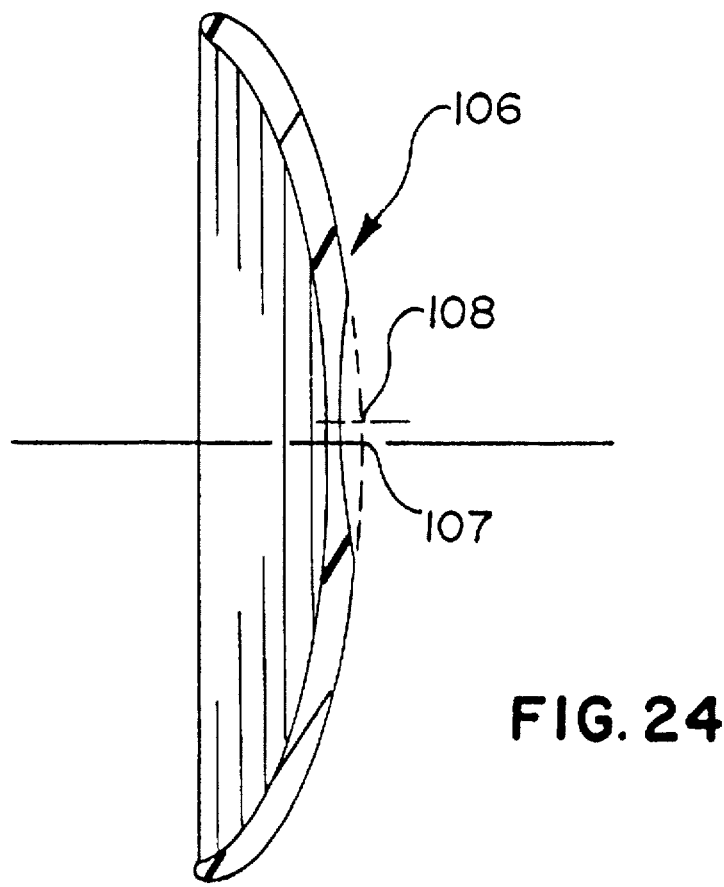
FIG. 24 is a cross-section view taken along lines 24—24 of FIG. 23.
Figure 25:
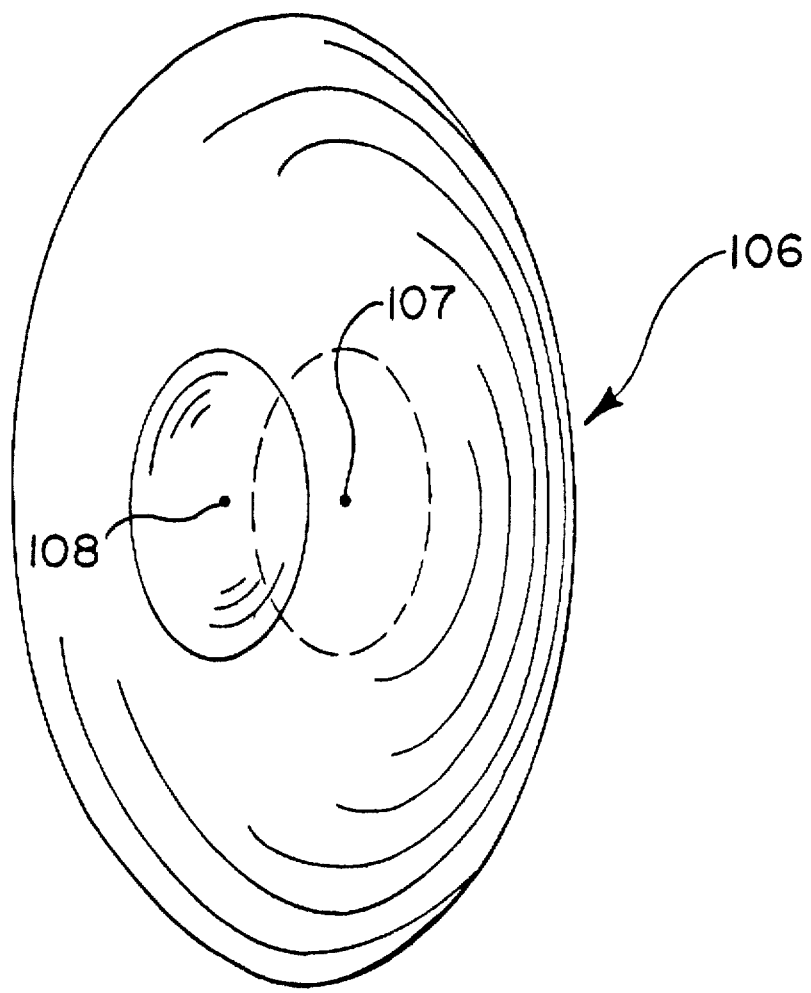
FIG. 25 is a perspective view of a contact lens illustrating decentered ablation.

Decentered ablation is possible with laser surgery. This decentration induces astigmatism. FIGS. 23–25 refer to contact lenses 106 which have been ablated in a decentrated manner. The lens 106 has a center 107. An ablation 108 of 6.0 mm is decentered 1.5 to 2 mm, not drawn to scale.

Figure 26:
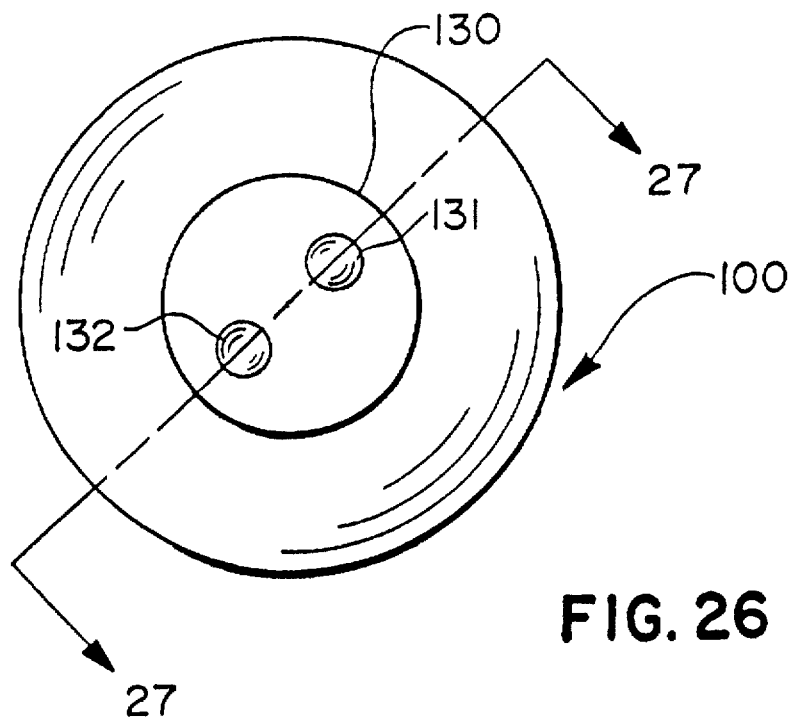
FIG. 26 is a front view of a contact lens showing central islands after ablation.
Figure 28:
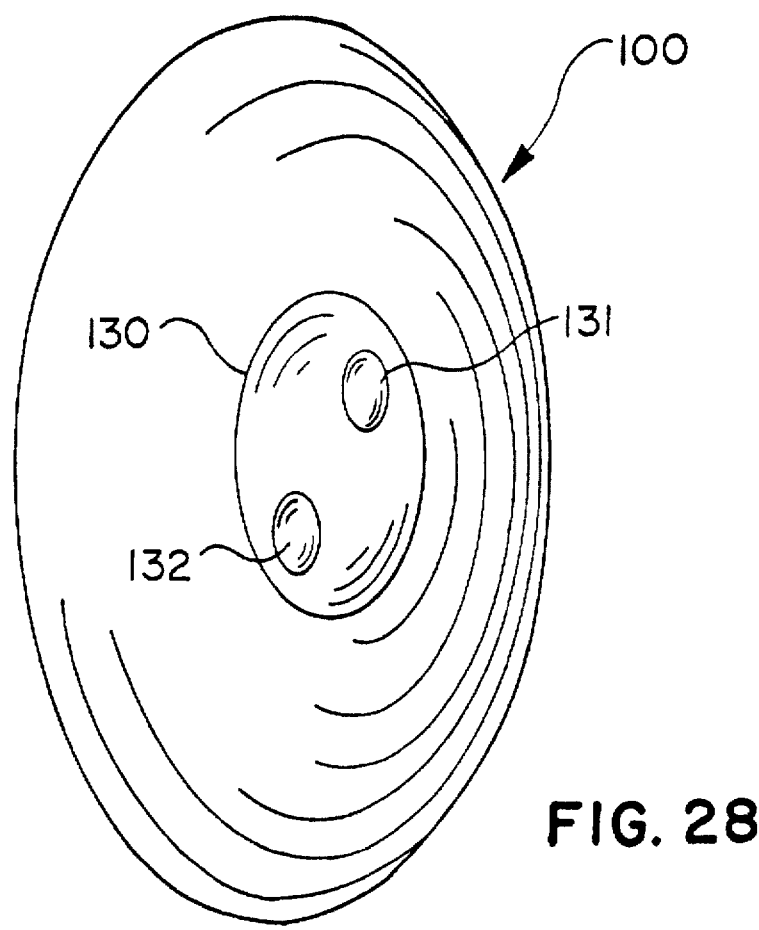
FIG. 28 is a perspective view of a contact lens illustrating central islands after ablation.
Figure 27:
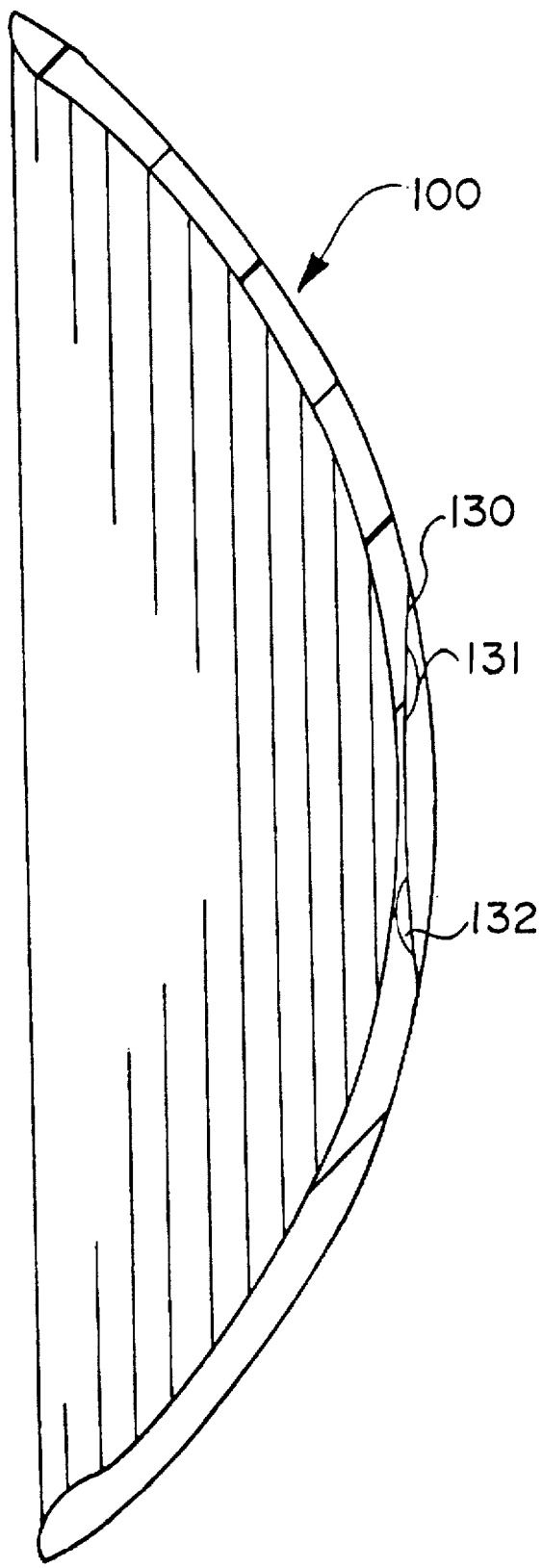
FIG. 27 is a cross-section taken along lines 27—27 of FIG. 26.

Ablation by PRK can result in central islands (FIGS. 26–28). Central islands are variations in contour of within the ablation area which do not receive adequate laser energy and remain steeper than surrounding treated areas. Also an inhomogeneous laser beam with areas of too much energy could give areas that are over treated or flattened too much 132. FIGS. 26–28 are lenses which have been surface-contoured to mimic ablation resulting in central islands. The area of correction 130 was ablated to produce smaller areas that remain steep 131. FIG. 28 is a section taken along lines 9—9 of FIG.26. The islands depict one or more randomly distributed areas of <1 mm to ≈2 mm with powers of +1 −1 diopter of that intended (−would mean a slightly too concave a contact lens anterior surface base curve (over treated) and a=would mean a slightly less concave (e.g., more convex) or anterior surface (slightly under treated or a central island). The central islands refer to areas that are too plus and are above the surrounding ablation and hence are termed islands.

Contact lenses tend to rotate while being worn. To stabilize the alignment of the lens so that the radial spokes, haze, decentration, etc. are stable, contact lenses may be stabilized by various design modifications that are in part standard practice for stabilizing current contact lenses for the correction of astigmatism. These modifications include making the lens thicker below (ballast), flattening of the rim of the lens so that the lower lid maintains orientation (truncation) or thinning of the periphery of the lens so that lid pressure maintains orientation (FIGS. 29 and 30).

Figure 29:
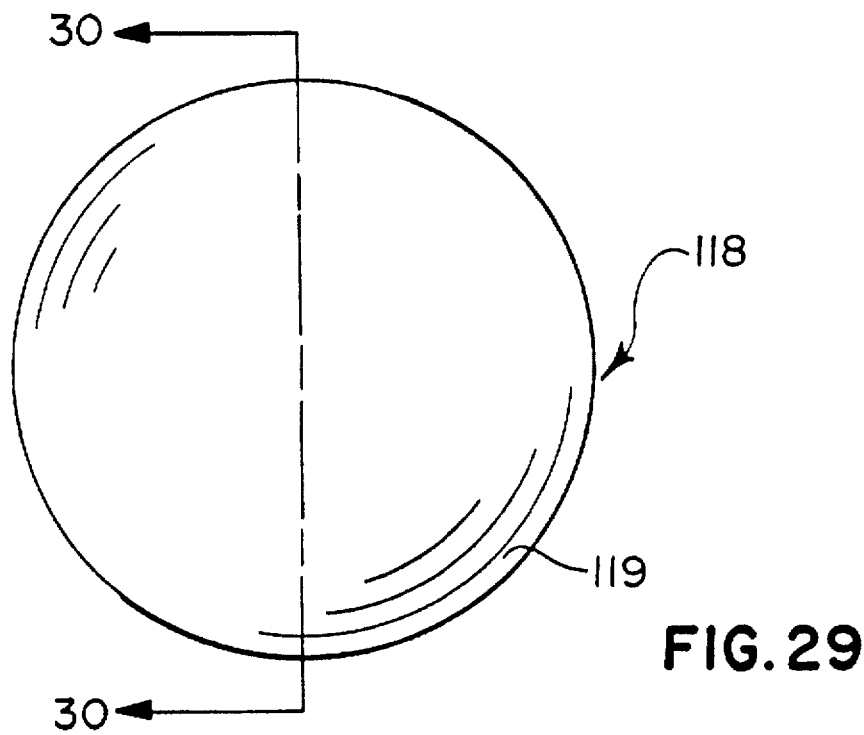
FIG. 29 is a front view of a toric contact lens.
Figure 30:
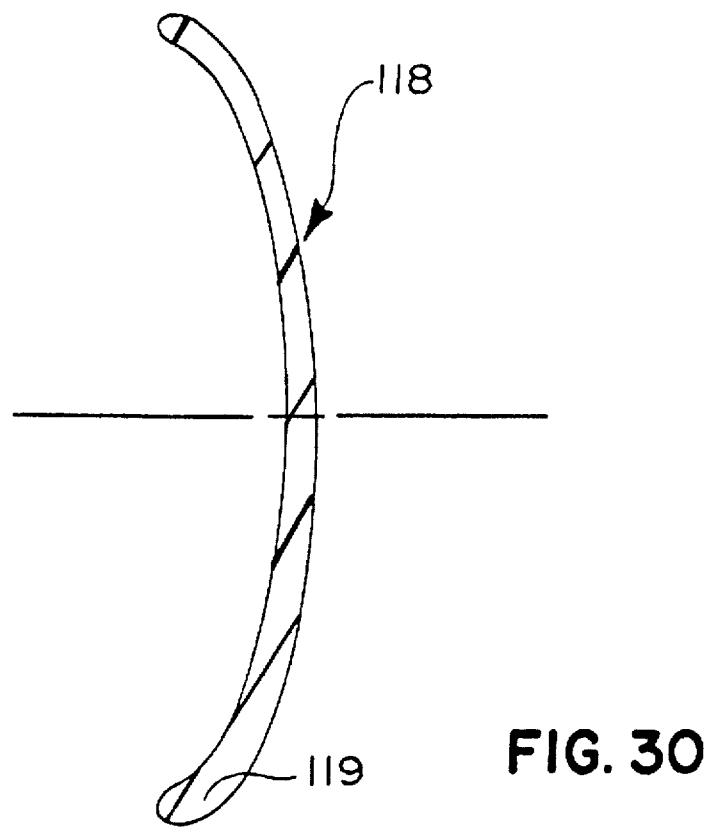
FIG. 30 is a cross-section taken along lines 30—30 of FIG. 29.

To preserve the orientation of the contact lens, the lens would be toric 118 (FIGS. 29 and 30). Orientation would be kept by the lens being thicker 119 below to weight the contact lens. Variation of the anterior surface may be used. For example, a front toric may be made where the lid pressure orientates the contact lens.

Figure 31:
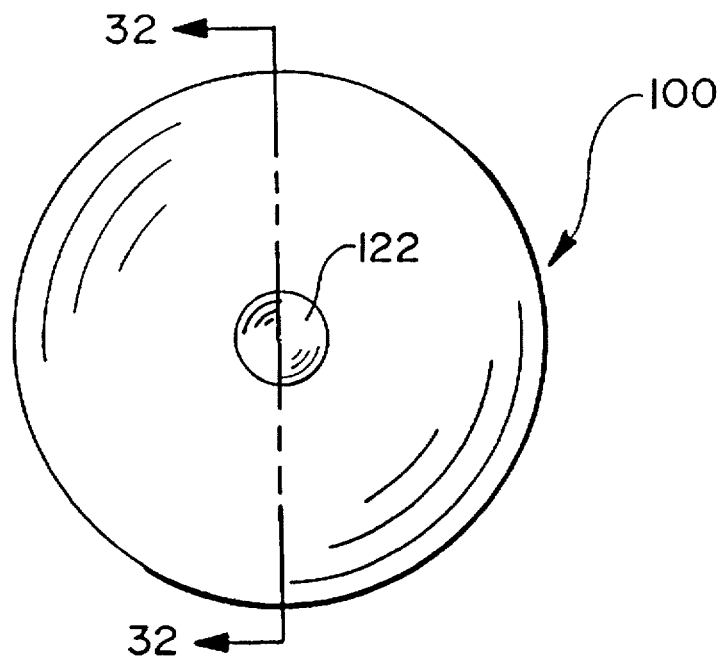
FIG. 31 is a view of a contact lens illustrating a small optical zone and resulting shallow cut.
Figure 32:
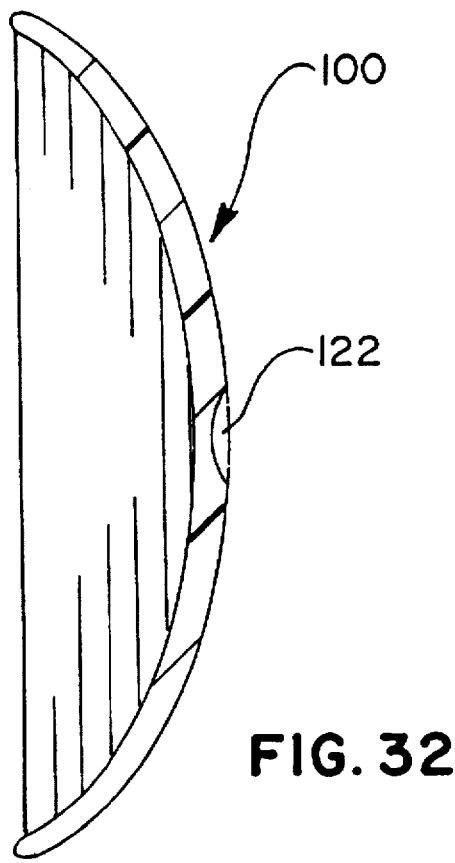
FIG. 32 is a section taken along lines 32—32 of FIG. 31
Figure 33:
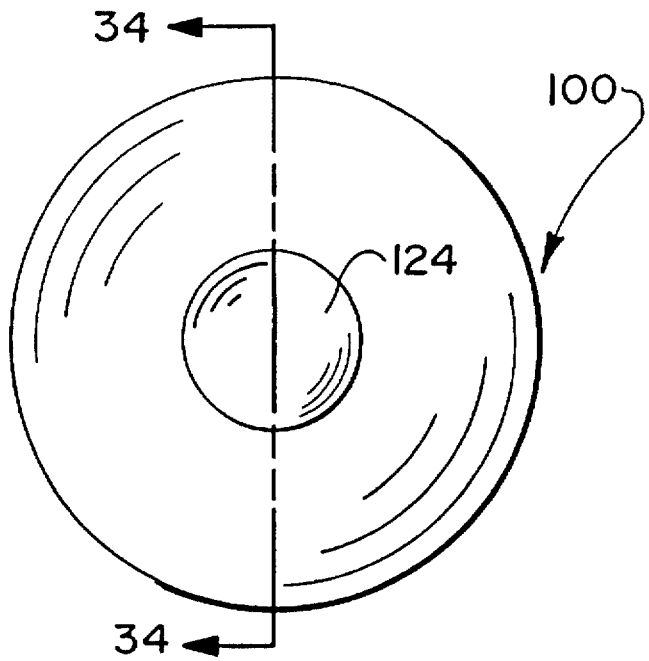
FIG. 33 is a view of a contact lens illustrating a larger optical zone and a deeper cut.
Figure 34:
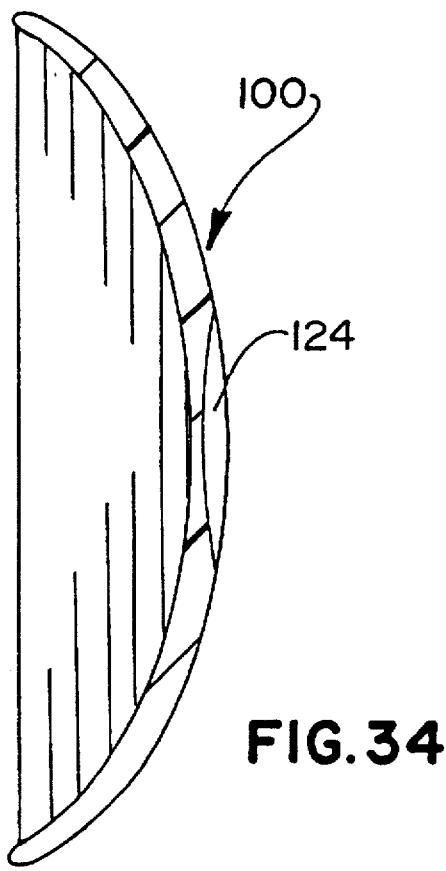
FIG. 34 is a section taken along lines 34—34 of FIG. 33.

With reference to FIGS. 31 to 34 the depth of the correction cut into the contact lens 100 would have to bare a relationship to the depth of the laser ablation of the cornea. The greater the correction and optical zone the greater the depth of cut. FIGS. 31 and 32 show a small optical zone and a resulting shallow cut 122. FIGS. 33 and 34 show that a larger optical zone requires a deeper cut 124 for the given power.

Figure 35:
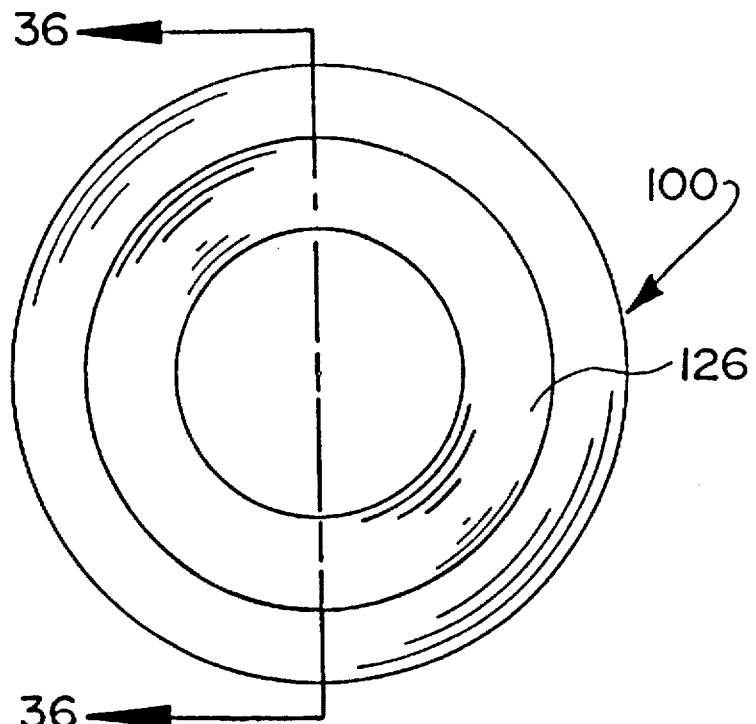
FIG. 35 is a front view of a contact lens to mimic ablation of the mid-periphery of the cornea.
Figure 36:
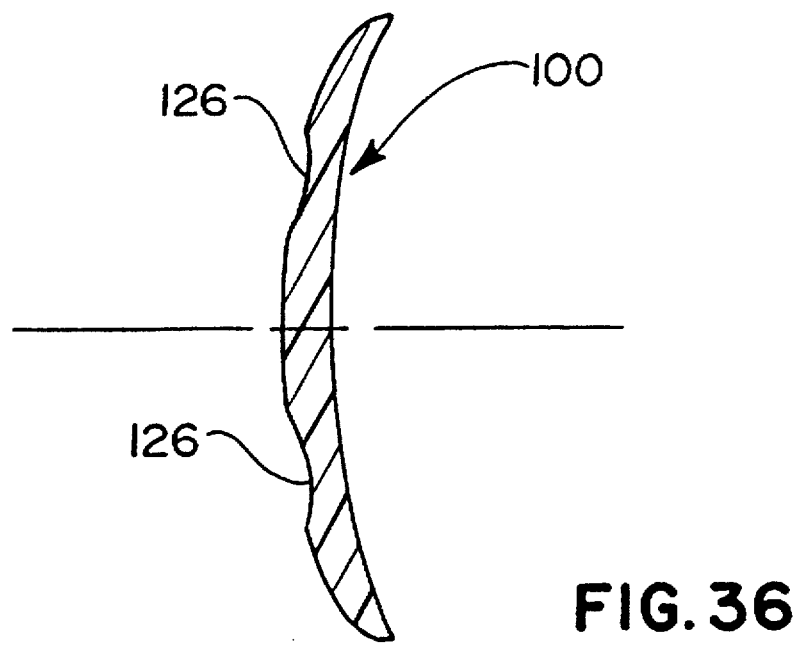
FIG. 36 is a cross-section taken along lines 36—36 of FIG. 35.

FIGS. 35–36 simulate hyperopic (far sighted) PRK correction. The midperiphery of the cornea is ablated to steepen the cornea, accordingly in fashioning a lens there would be a haze area in the para central to midperiphery of the cornea. In the lens 100 midperiphery steepening 126 is illustrated.

The above concepts can also be applied to hyperopic laser corrections where the central cornea is left steeper and the peripheral cornea treated to increase the base curve of the cornea.

Over and under corrections are simulated with contact lenses that are too strong or too weak for the patient's actual refraction.

Figure 39:
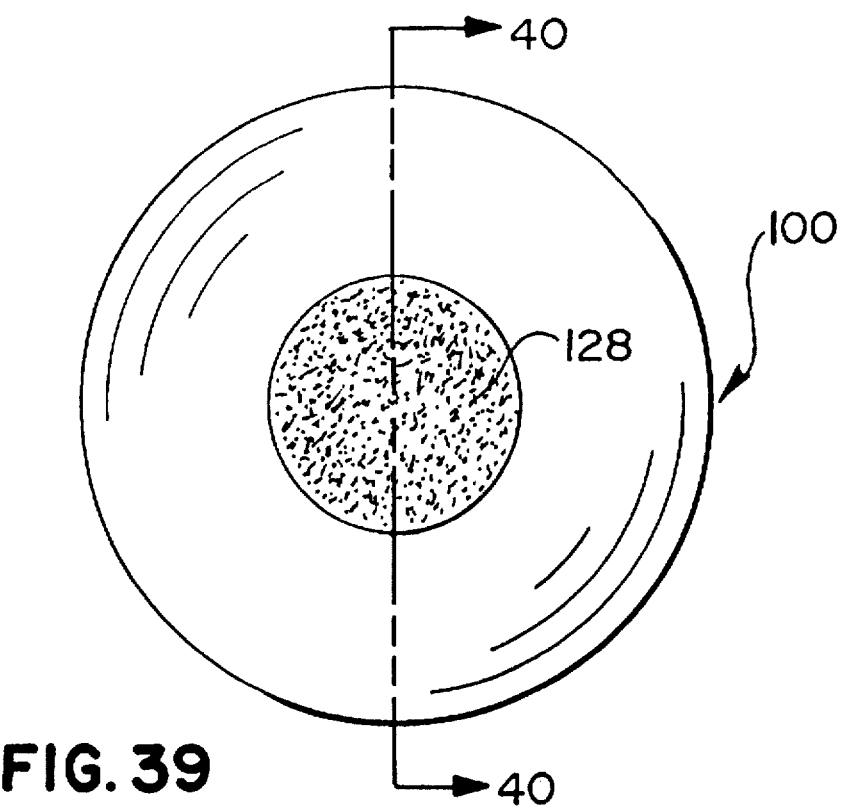
FIG. 39 is a view of a contact lens illustrating haze markings sandwiched between the anterior and posterior sections of the lens.
Figure 40:
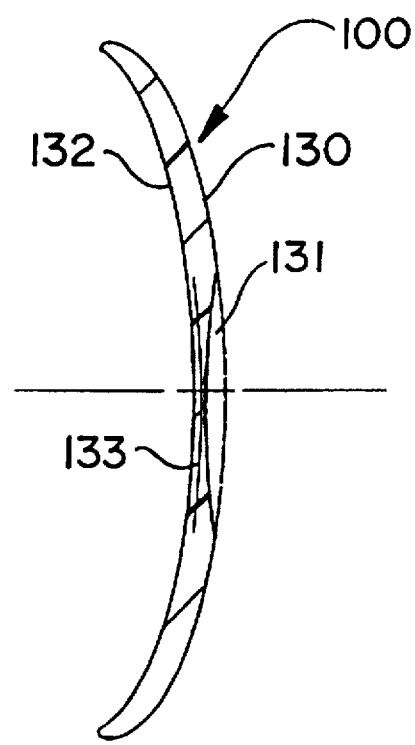
FIG. 40 is a section taken along lines 40—40 of FIG. 39.

LASIK problems could be simulated with the present invention (FIGS. 37–40). In LASIK a cap or flap of anterior cornea is generated with an automated blade and laser treatment performed in the corneal stromal bed. Haze 128 at the generated interface could be simulated. In this embodiment of the invention, the anterior surface 130 of the contact lens 100 is contoured 131 and markings are placed on the posterior surface 132 of the contact lens 100 (FIGS. 37—38) or haze markings 128 are sandwiched 133 between anterior 130 and posterior 132 sections of the lens (FIGS. 39–40).

Figure 41:
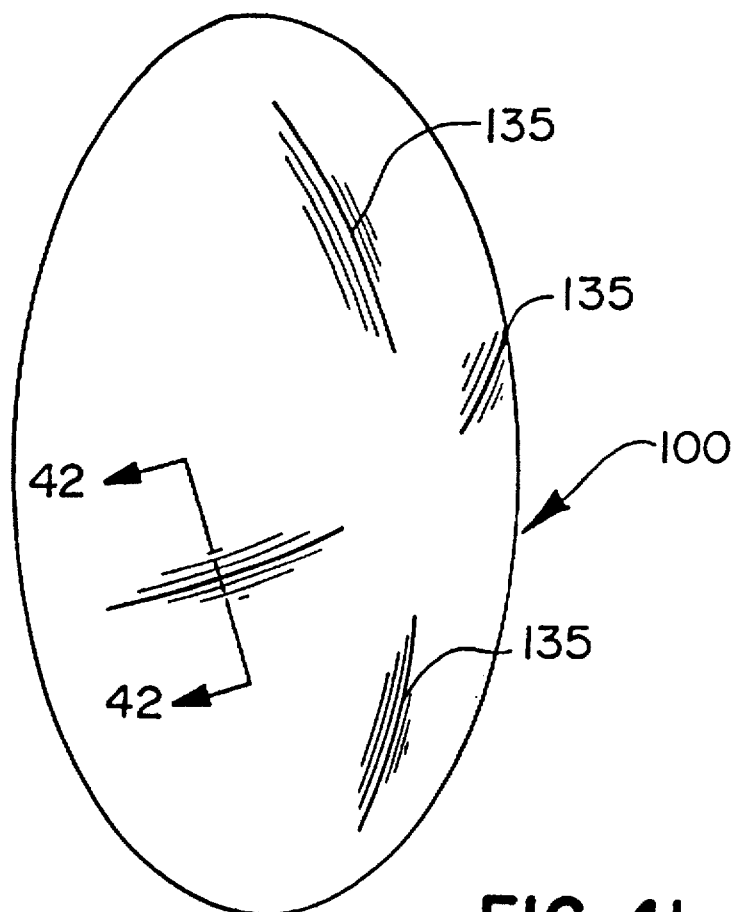
FIG. 41 is a view illustrating a four incision radial keratotomy (RK).
Figure 42:
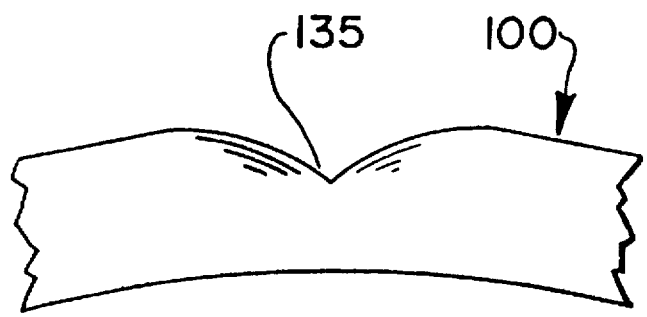
FIG. 42 is a cross-section taken along lines 42—42 of FIG. 41 with part of the lens broken away for ease of illustration.

FIGS. 41 and 42 illustrate a four incision 135 radial keratotomy (RK). There is steepening along the incisions and flattening between the incisions and along the central cornea. The flatter area is shown in the center of the lens and between the incisions.

Figure 43:
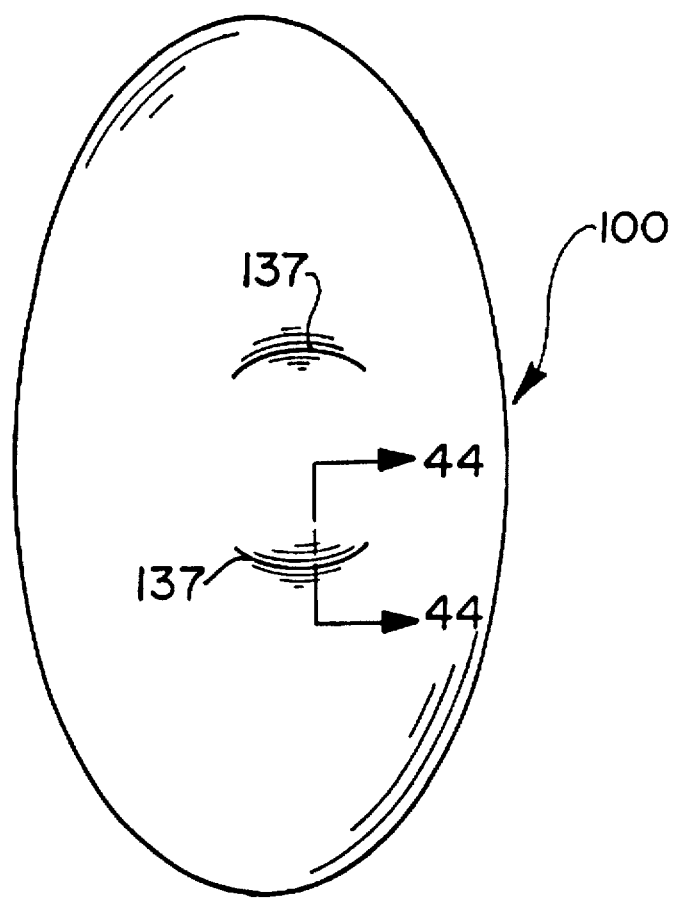
FIG. 43 is a view illustrating a two incision astigmatic keratotomy.
Figure 44:
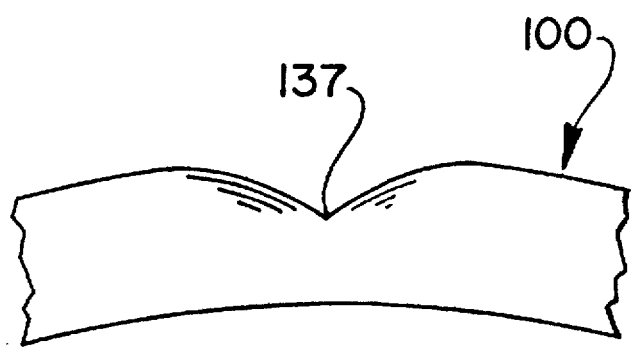
FIG. 44 is a cross-section taken along lines 44—44 of FIG. 43 with part of the lens broken away for ease of illustration.

FIGS. 43 and 44 illustrate a lens which would be used after a two incision 137 AK (astigmatic keratotomy). There is flattening in the meridian of the incision and steepening 90° away from the incision.

Obviously, many modifications may be made without departing from the basic spirit of the present invention. Accordingly, it will be appreciated by those skilled in the art that within the scope of the appended claims, the invention may be practiced other than has been specifically described herein.

We claim:

1. A method for obtaining informed consent from a patient prior to ophthalmologic surgery comprising applying to the eye or eyes of said patient contemplating ophthalmologic surgery, a contact lens whose anterior surface has been contoured to mimic the contours of the cornea of the eye which may result from said ophthalmologic surgery and then obtaining informed consent from said patient.

2. A method for obtaining informed consent from a patient prior to ophthalmologic laser surgery comprising the steps of determining the area and depth of ablation of said ophthalmologic laser surgery on the cornea, molding, lathe cutting or laser contouring the anterior surface of a contact lens with the same area and depth of ablation which would result from said ophthalmologic laser surgery, applying the contoured lens to the eye of said patient and then obtaining informed consent from said patient prior to said ophthalmologic laser surgery.

3. In a method of obtaining informed consent from a patient prior to surgery, the improvement comprising fitting the patient with a virtual reality device which has been programmed to simulate the ophthalmologic anomaly which might be experienced by the patient as a result of said surgery and obtaining informed consent from said patient.

* * * * *